US005837453A

United States Patent [19]
Harley et al.

[11] Patent Number: 5,837,453
[45] Date of Patent: *Nov. 17, 1998

[54] TELOMERASE ACTIVITY ASSAYS

[75] Inventors: Calvin Bruce Harley, Palo Alto; Nam Woo Kim, San Jose; Scott Lawrence Weinrich, San Francisco, all of Calif.

[73] Assignee: Geron Corporation, Menlo Park, Calif.

[*] Notice: The term of this patent shall not extend beyond the expiration date of Pat. No. 5,629,154.

[21] Appl. No.: 482,132

[22] Filed: Jun. 7, 1995

Related U.S. Application Data

[63] Continuation-in-part of Ser. No. 315,214, Sep. 28, 1994, Pat. No. 5,629,154, which is a continuation-in-part of Ser. No. 255,774, Jun. 7, 1994, which is a continuation-in-part of Ser. No. 153,051, Nov. 12, 1993, Pat. No. 5,645,987, and Ser. No. 151,477, Nov. 12, 1993, each is a continuation-in-part of Ser. No. 60,952, May 13, 1993, Pat. No. 5,695,932, which is a continuation-in-part of Ser. No. 38,706, Mar. 24, 1993, Pat. No. 5,489,508, which is a continuation-in-part of Ser. No. 882,438, May 13, 1992, abandoned.

[51] Int. Cl.$^6$ .............................. C12Q 1/68; C12P 19/34; C07H 21/02; C07H 21/04
[52] U.S. Cl. .............................. 435/6; 435/91.2; 435/174; 536/23.1; 536/24.3; 536/24.33; 530/300; 530/350
[58] Field of Search ................................. 536/23.1, 24.3, 536/24.33, 26.6; 435/6, 91.2, 174; 530/300, 350

[56] References Cited

U.S. PATENT DOCUMENTS

| | | | |
|---|---|---|---|
| 4,424,279 | 1/1984 | Bohn et al. | 435/534 |
| 4,737,454 | 4/1988 | Dattagupta . | |
| 5,041,199 | 8/1991 | Di Franco | 204/181.5 |
| 5,124,246 | 6/1992 | Urdea et al. . | |
| 5,137,031 | 8/1992 | Gurguis | 128/771 |
| 5,188,963 | 2/1993 | Stapleton . | |
| 5,196,306 | 3/1993 | Bobrow et al. . | |
| 5,231,015 | 7/1993 | Cummins et al. | 435/91 |
| 5,310,652 | 5/1994 | Gelfand et al. . | |
| 5,334,499 | 8/1994 | Burdick et al. | 435/6 |
| 5,369,003 | 11/1994 | Reischl et al. . | |
| 5,413,924 | 5/1995 | Kosak et al. . | |
| 5,415,758 | 5/1995 | Comeau et al. | 204/299 R |
| 5,451,500 | 9/1995 | Stapleton | 435/6 |
| 5,474,916 | 12/1995 | Reischl et al. . | |
| 5,489,508 | 2/1996 | West et al. . | |
| 5,491,063 | 2/1996 | Fisher et al. . | |
| 5,538,848 | 7/1996 | Livak et al. . | |
| 5,639,613 | 6/1997 | Shay et al. . | |
| 5,645,986 | 7/1997 | West et al. . | |
| 5,648,215 | 7/1997 | West et al. . | |

FOREIGN PATENT DOCUMENTS

| | | |
|---|---|---|
| 2259138 | 3/1993 | United Kingdom . |
| 2294322 | 4/1996 | United Kingdom . |
| 9304546 | 5/1993 | WIPO . |
| WO 93/23572 | 11/1993 | WIPO . |
| 9408053 | 4/1994 | WIPO . |

OTHER PUBLICATIONS

Blackburn et al., Recognition and Elongation of Telomeres by Telomerase, Genome, 31:553–560 (1989).
Blackburn, Structure and Function of Telomeres, Nature, 350:569–573 (May 1991).
Counter et al., Stabilization of Short Telomeres and Telomerase Activity Accompany Immortalization of Epstein–Barr Virus–Transformed Human B Lymphocytes, Journal of Virology, 68(5):3410–3414 (May 1994).
Counter et al., Telomerase Activity in Normal Leukocytes and in Hematologic Malignancies, Blood, 85(9):2315–2320 (May 1995).
Counter et al., Telomerase Activity in Human Ovarian Carcinoma, Proc. Natl. Acad. Sci., 91:2900–2904 (Apr. 1994).
Counter et al., Telomere Shortening Associated with Chromosome Instability is Arrested in Immortal Cells Which Express Telomerase Activity, The EMBO Journal, 11(5):1921–1929 (1992).
Greider and Blackburn, The Telomere Terminal Transferase of Tetrahymena Is a Ribonucleoprotein Enzyme with Two Kinds of Primer Specificity, Cell, 51:887–898 (1987).
Greider et al., A Telomeric Sequence in the RNA of Tetrahymena Telomerase Required for Telomere Repeat Synthesis, Nature, 337:331–337 (Jan. 1989).
Greider et al., Identification of a Specific Telomere Terminal Transferase Activity in Tetrahymena Extracts, Cell, 43:405–413 (Dec. 1985).
Greider, Telomerase Is Processive, Molecular and Cellular Biology, 11;4572–4580 (Sep. 1991).
Harley et al., Telomere Loss: Mitotic Clock or Genetic Time Bomb?, Mutation Research, 256:271–282 (1991).
Harley et al, Telomeres Shorten During Ageing of Human Fibroblasts, Nature, 345:458–460 (May 1990).
Hiyama et al., Length of Telomeric Repeats in Neuroblastoma: Correlation with Prognosis and Other Biological Characteristics, Jpn. J. Cancer Res., 83:159–164 (1992).
Kim et al., Specific Association of Human Telomerase Activity with Immortal Cells and Cancer, Science, 266:2011–2015 (Dec. 1994).
Morin, The Human Telomere Terminal Transferase Enzyme is a Ribonucleoprotein That Synthesizes TTAGGG Repeats, Cell, 59:521–529 (Nov. 1989).
Shay et al., Loss of Telomeric DNA During Aging May Predispose Cells to Cancer, International Journal of Oncology, 3:559–563 (1993).

(List continued on next page.)

Primary Examiner—W. Gary Jones
Assistant Examiner—Dianne Rees
Attorney, Agent, or Firm—Melya J. Hughes; Richard L. Neeley; Kevin R. Kaster

[57] ABSTRACT

Telomerase activity in a sample can be measured using a two reaction protocol involving telomerase substrate and primer extension steps. The presence of telomerase activity in a human somatic tissue or cell sample is positively correlated with the presence of cancer and can be used to diagnose the course of disease progression in a patient.

30 Claims, 1 Drawing Sheet

OTHER PUBLICATIONS

Windle, and McGuire, Telomeres: The Long and the Short of It, Proceedings of the American Association for Cancer Research, Eighty–Third Annual Meeting of the American Association for Cancer Research, 33:594–595 (Mar. 1992).

Eck SL, Nabel GJ, "Antisense oligonucleotides for therpeutic intervention" (1991) *Curr Opin Biotechnol* 2(6):897–904.

Morin et al, Nature 353: 454–456, 1991.

Barany et al, PNAS 88: 189–193, 1991.

Allsopp et al., (1992) "Telomere Length Predicts Replicative Capacity of Human Fibroblasts," *Proc. Natl. Acad. Sci. USA* 89:10114–10118.

Baird et al., (1995) "Mechanism Underlying Telomere Repeat Turnover Revealed by Hypervariable Variant Repeat Distribution Patterns in the Human Xp/Yp Telomere" *EMBO J.* 14:5433–5443.

Blackburn, (1984) "The Molecular Structure of Centromeres and Telomeres" *Annual Reviews in Biochemistry* 53:163.

Cech, (1988) "Ribozymes and Their Medical Implications" *JAMA* 26):3030.

Cooke and Smith, (1986), "Variability at the Telomeres of the Human X/Y Psuedoautosomal Region" *CSHSQB* LI:213.

Cotten, (1990) "The In Vivo Application of Ribosomes," *Trends in Biotechnology* 8:174–178.

Gall, (1990) "Tying Up Loose Ends" *Nature* 344:108.

Goldstein, (1990) "Replicative Senescence: The Human Fibroblast Comes of Age" *Science* 249:1129.

Gottschling et al., (1990) "Position Effect at *S. cerevisiae* Telomeres: Reversible Repression of Pol II Transcription" *Cell* 63:751.

Gray et al., (1991) "Cloning and Expression of Genes for the Oxytricha Telomere–binding Protein Specific Subunit Interactions in the Telomeric Complex" *Cell* 67:807.

Greider, (1990) "Telomeres, Telomerase and Senescence" *Bioessays* 12:363.

Greider, (1991) "Chromosome First Aid" *Cell* 67:645.

Ham and McKeehan, et al., (1979) "Media and Growth Requirements" *Methods in Enzymology* LVIII:44.

Harley et al., (1992) "The Telomere Hypothesis of Cellular Aging," *Experimental Gerontology* 27:375–382.

Harrington and Greider, (1991) "Telomerase Primer Specificity and Chromosome Healing" *Nature* 353:451.

Hayflick and Moorhead, (1961) "The Serial Cultivation of Human Diploid Cell Strains" *Experimental Cell Research* 25:585.

Henderson et al., (1990) "Telomere G–strand Structure and Function Analyzed by Chemical Protection, Base Analogue Substitution, and Utilization by Telomerase In Vitro" *Biochemistry* 29:732.

Ijdo et al., (1991) "Improved Telomere Detection Using a Telomere Repeat Probe $(TTAGGG)_n$ Generated by PCR" *Nucleic Acids Research* 19: 4780.

Innis et al., In PRC Protocols A Guide to Methods and Applications, Chapters 1, 2 and 3, 1992 (vol. #, p. # not relevant).

Jankovic et al., (1991) "Telomere Loss and Cancer" *Nature* 350:197.

Klingelhutz et al., (1994) "Restoration of Telomeres in Human Papoillomavirus–Immortalized Human Anogenital Epithelial Cells," *Molecular and Cellular Biology* 14:961–969.

Kwoh et al., (1989) "Transcription Based Amplification System and Detection of Amplified Human Immunodeficiency Virus Type 1 with a Bead–Based Sandwich Hybridization Format" *Proc. Natl. Acad. Sci. USA* 86:1173–1177.

Lundblad and Szostak, (1989) "A Mutant With a Defect in Telomere Elongation Leads to Senescence in Yeast" *Cell* 57:633.

Muller et al., (1991) "New Telomere Formation After Developmentally Regulated Chromosomal Breakage During the Process of Chromosome Diminution in *Ascaris lumbricoides*" *Cell* 67:815.

Ohno, (1979) "Strict Relationship Between Dialyzed Serum Concentration and Cellular Life Span In Vitro" *Mechanism of Aging and Development* 11:179.

Olovnikov (1973) "A Theory of Marginotomy" *J. Theoretical Biology* 41:181.

Smith and Whitney, (1980), "Intraclonal Variation in Proliferative Potential of Human Diploid Fibroblastsistochastic Mechanisms for Cellular Aging" *Science* 207:82.

Starling et al., (1990) "Extensive Telomere Repeat Arrays in Mouse are Hypervariable" *Nucleic Acids Research* 18:6881.

Strahl and Blackburn, (1994) "The Effects of Nucleoside Analogs on Telomerase and Telomeres in Tetrahymena" *Nucleic Acids Research* 22:893–900.

Szostak, (1989) "The Beginning of the Ends" *Nature* 337:303.

Wang and Zakian, (1990) "Telomere–Telomere Recombination Provides an Express Pathway for Telomere Acquisition" *Nature* 345:456.

Weber et al., (1990) "Characterization and Organization of DNA Sequences Adjacent to the Human Telomere Associated Repeat $(TTAGGG)_n$," *Nucleic Acids Research* 18:3353–3361.

Wilkie et al., (1990) "A Truncated Human Chromosome 16 Associated with Alpha Thalassaemia is Stabilized by Addition of Telomeric Repeat $(TTAGGG)_n$." *Nature* 346(6287):868–871.

Yu et al., (1990) "In vivo Alteration of Telomere Sequences and Senescence Caused by Mutated Tetrahymena Telomerase RNAs" *Nature* 344:126.

Yu and Blackburn, (1991) "Developmentally Programmed Healing of Chromosomes by Telomerase in Tetrahymena" *Cell* 67:823.

Zahler et al., (1991) "Inhibition of Telomerase by G–quartet DNA Structures" *Nature* 350:718.

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:1:

```
CCCTTACCCT TACCCTTACC CTAA                                            24
```

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:2:

```
GCGCGGCTTA CCCTTACCCT TACCCTAACC                                      30
```

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:3:

```
AATCCGTCGA GCAGAGTT                                                   18
```

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:4:

CCCAATCCGT CGAGCAGAGT TAG    23

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:5:

TAACTCTGCT CGACGGATTC CC    22

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:6:

GGGTAACCCT AACCCTAACC C    21

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:7:

GGTTAGGGTT AGGGTTAAA    19

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:8:

GTTAGGGTTA GGGTTAGG    18

( 2 ) INFORMATION FOR SEQ ID NO:9:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: synthetic ( i i i ) HYPOTHETICAL: NO ( i v ) ANTI-SENSE: NO ( x i ) SEQUENCE DESCRIPTION: SEQ ID NO:9:

TTAGGGTTAG GGTTAGGG                       18

( 2 ) INFORMATION FOR SEQ ID NO:10:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:10:

CCCTAACCCT AACCCTAA                      18

( 2 ) INFORMATION FOR SEQ ID NO:11:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:11:

CCCTAACCCT AACCCTAACC CTAA                 24

( 2 ) INFORMATION FOR SEQ ID NO:12:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:12:

GCGCGGCTAA CCCTAACCCT AACC                 24

( 2 ) INFORMATION FOR SEQ ID NO:13:

( i ) SEQUENCE CHARACTERISTICS:
    ( A ) LENGTH: 47 base pairs (B) TYPE: nucleic acid
(C) STRANDEDNESS: single
(D) TOPOLOGY: linear (i i) MOLECULE TYPE: DNA (synthetic)

(i i i) HYPOTHETICAL: NO (i v) ANTI-SENSE: NO (x i) SEQUENCE DESCRIPTION: SEQ ID NO:13:

AATCCGTCGA GCAGAGTTAG CCCGGTTAGG GTTAGGGTTA GCCGCGC    47

(2) INFORMATION FOR SEQ ID NO:14:

(i) SEQUENCE CHARACTERISTICS:
(A) LENGTH: 62 base pairs
(B) TYPE: nucleic acid
(C) STRANDEDNESS: single
(D) TOPOLOGY: linear (i i) MOLECULE TYPE: DNA (synthetic)

(i i i) HYPOTHETICAL: NO (i v) ANTI-SENSE: NO (x i) SEQUENCE DESCRIPTION: SEQ ID NO:14:

AATCCGTCGA GCAGAGTTAG GGTTAGGGTT AGGGTTAGGG TTAGGGTTAG GGTTAGGGTT AG    62

(2) INFORMATION FOR SEQ ID NO:15:

(i) SEQUENCE CHARACTERISTICS:
(A) LENGTH: 30 base pairs
(B) TYPE: nucleic acid
(C) STRANDEDNESS: single
(D) TOPOLOGY: linear (i i) MOLECULE TYPE: DNA (synthetic)

(i i i) HYPOTHETICAL: NO (i v) ANTI-SENSE: NO (x i) SEQUENCE DESCRIPTION: SEQ ID NO:15:

CCCTAACCCT AACCCTAACC CTAACCCTAA    30

(2) INFORMATION FOR SEQ ID NO:16:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA (synthetic)

(i i i) HYPOTHETICAL: NO (i v) ANTI-SENSE: NO (x i) SEQUENCE DESCRIPTION: SEQ ID NO:16:

TTTCCCTTTC CCTTTCCC    18

(2) INFORMATION FOR SEQ ID NO:17:

(i) SEQUENCE CHARACTERISTICS:
(A) LENGTH: 24 base pairs
(B) TYPE: nucleic acid
(C) STRANDEDNESS: single
(D) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:17:

TTTCCCTTTC CCTTTCCCTT TCCC         24

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:18:

CTTACCCTTA CCCTTACCCT AACC         24

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:19:

AACTCTGCTC GACGGATT         18

( 2 ) INFORMATION FOR SEQ ID NO:20:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:20:

GCCCAATCCG TCGAGCAGAG TTAG         24

( 2 ) INFORMATION FOR SEQ ID NO:21:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO

-continued (iv) ANTI-SENSE: NO (xi) SEQUENCE DESCRIPTION: SEQ ID NO:21:

CTAACTCTGC TCGACGGATT GGGC 24

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (xi) SEQUENCE DESCRIPTION: SEQ ID NO:22:

CTCGGTACCA AGCTTCTAAC CCTAACCCTA ACC 33

TELOMERASE ACTIVITY ASSAYS

CROSS-REFERENCE TO RELATED APPLICATIONS

The present application is a continuation-in-part of U.S. patent application Ser. No. 08/315,214, filed 28 Sep. 1994 now U.S. Pat. No. 5,629,154, which is a continuation-in-part of Ser. No. 08/255,774, filed 7 Jun. 1994, which is a continuation-in-part of Ser. Nos. 08/151,477 and 08/153,051 now U.S. Pat. No. 5,645,986, both of which were filed 12 Nov. 1993, which are continuation-in-part of Ser. No. 08/060,952, filed 13 May 1993, now U.S. Pat. No. 5,695,932 which is a continuation-in-part of Ser. No. 08/038,766, filed 24 Mar. 1993 now U.S. Pat. No. 5,489,508, which is a continuation-in-part of now abandoned Ser. No. 07/882,438, filed 13 May 1992. Each of the foregoing patent applications is incorporated herein by reference.

This invention described herein was made with Government support under a grant from the Department of Health and Human Services. The Government has certain rights in this invention

INTRODUCTION

1. Technical Field

The present invention relates to telomerase, a ribonucleoprotein enzyme involved in telomere DNA synthesis, and provides assays and materials for identifying and measuring telomerase activity. The invention relates to the fields of molecular biology, chemistry, pharmacology, and medical diagnostic and prognostic technology.

2. Background

Telomeres are specialized structures at the ends of eukaryotic chromosomes and appear to function in chromosome stabilization, positioning, and replication (Blackburn and Szostak, 1984, *Ann. Rev. Biochem.* 53:163–194; Zakian, 1989, *Ann. Rev. Genetics* 23:579–604; Blackburn, 1991 *Nature* 350:569–573). In all vertebrates, telomeres consist of hundreds to thousands of tandem repeats of 5'-TTAGGG-3' sequence and associated proteins (Blackburn, 1991; Moyzis et al., 1988, *Proc. Natl. Acad. Sci.* 85:6622–6626). Southern blot analysis of chromosome terminal restriction fragments (TRF) provides the composite lengths of all telomeres in a cell population (Harley et al., 1990, *Nature* 345:458–460; Allsopp et al., 1992, *Proc. Natl. Acad. Sci. USA* 89:10114–10118; Vaziri et al., 1993, *Am. J. Human Genetics* 52:661–667). In all normal somatic cells examined to date, TRF analysis has shown that the chromosomes lose about 50–200 nucleotides of telomeric sequence per cell division, consistent with the inability of DNA polymerase to replicate linear DNA to the ends (Harley et al., 1990; Allsopp et al., 1992; Vaziri et al., 1993; Watson, 1972, *Nature New Biology* 239:197–201).

This shortening of telomeres has been proposed to be the mitotic clock by which cells count their divisions (Harley, 1991, *Mut. Res.* 256:271–282), and a sufficiently short telomere(s) may be the signal for replicative senescence in normal cells (Allsopp et al., 1992; Vaziri et al., 1993; Hastie et al., 1990, *Nature* 346:866–868; Lindsey et al., 1991, *Mut. Res.* 256:45–8; Wright and Shay, 1992, *Trends Genetics* 8:193–197). In contrast, the vast majority of immortal cells examined to date shows no net loss of telomere length or sequence with cell divisions, suggesting that maintenance of telomeres is required for cells to escape from replicative senescence and proliferate indefinitely (Counter et al., 1992, *EMBO* 11:1921–1929; Counter et al., 1994, *Proc. Natl. Acad. Sci. USA* 91:2900–2940).

Telomerase, a unique ribonucleoprotein DNA polymerase, is the only enzyme known to synthesize telomeric DNA at chromosomal ends using as a template a sequence contained within the RNA component of the enzyme (Greider and Blackburn, 1985, *Cell* 43:405–413; Greider and Blackburn, 1989, *Nature* 337:331–337; Yu et al., 1990, *Nature* 344:126–132; Blackburn, 1992, *Ann. Rev. Biochem.* 61:113–129). With regard to human cells and tissues, telomerase activity has been identified in immortal cell lines and in ovarian carcinoma but has not been detected at biologically significant levels (that required to maintain telomere length over many cell divisions) in mortal cell strains or in normal non-germline tissues (Counter et al., 1992; Counter et al., 1994; Morin, 1989, *Cell* 59:521–529). Together with TRF analysis, these results suggest telomerase activity is directly involved in telomere maintenance, linking this enzyme to cell immortality.

Methods for detecting telomerase activity, as well as for identifying compounds that regulate or affect telomerase activity, together with methods for therapy or diagnosis of cellular senescence and immortalization by controlling or measuring telomere length and telomerase activity, have also been described. See PCT patent publication No. 93/23572, published Nov. 25, 1993, incorporated herein by reference. The identification of compounds affecting telomerase activity provides important benefits to efforts at treating human disease. Compounds that inhibit telomerase activity can be used to treat cancer, as cancer cells express and require telomerase activity for immortality, and normal human somatic cells do not express telomerase activity at detectable levels. Compounds that stimulate or activate telomerase activity van be used to treat age-related diseases and other conditions relating to cell senescence.

Current methods for assaying telomerase activity in cell samples rely on the incorporation of radioactively labeled nucleotides into a telomerase substrate (Morin, 1989). The conventional assay uses an oligonucleotide substrate, a radioactive deoxyribonucleotide triphosphate (dNTP) for labeling, and gel electrophoresis for resolution and display of products. Because telomerase stalls and can release the DNA after adding the first G in the 5'-TTAGGG-3' telomeric repeat, the characteristic pattern of products on the gel is a six nucleotide ladder of extended oligonucleotide substrates. The phase of the repeats depends on the 3'-end sequence of the substrate; telomerase recognizes where the end is in the repeat and synthesizes accordingly to yield contiguous repeat sequences. Although telomeric sequence oligonucleotides are efficient in vitro substrates, telomerase will also synthesize repeats using substrates comprising non-telomeric DNA sequences.

Using such methods, scientists have found that reliable telomerase extraction by hypotonic swelling and physical disruption of cells requires at least $10^7$–$10^8$ cells and that the extraction efficiency varies between cell types (Counter et al., 1992; Morin, 1989). There remains a need for telomerase activity assays with increased sensitivity, speed, and efficiency of detecting telomerase activity as compared to the conventional assay and this invention meets that need.

SUMMARY OF THE INVENTION

It is an object of the invention to provide a readily reproducible assay system for detecting telomerase activity, which is simple enough to use in the smaller (or low budget) clinical setting, but has the potential for high throughput using readily available robotics technology. The assays can be used as diagnostic or prognostic aids, or for the identification, screening and development of molecules that act as telomerase inhibitors. The present invention also provides related reagents and materials useful for practice of the method. The method comprises the steps of:

(a) collecting a cell sample;

(b) incubating the cell sample with a telomerase substrate lacking a telomeric repeat sequence to allow telomerase to catalyze extension of the telomerase substrate;

(c) adding to the cell sample a primer comprising a sequence sufficiently complementary to a telomeric repeat to hybridize specifically thereto under conditions such that if an extended telomerase substrate is present in the cell sample mixture, the primer will hybridize to the extended telomerase substrate and extend to form a complementary copy of the extended telomerase substrate; and (d) correlating presence of telomerase activity in the cell sample with presence of duplex DNA molecules comprising an extended telomerase substrate bound to an extended primer and absence of telomerase activity in the cell sample with absence of the duplex DNA molecules.

The present invention also provides reagents, kits, and related methods and materials useful in the practice of the invention. One such related method involves the extraction of telomerase activity from a cell sample using, for example, a buffer that comprises a non-ionic and/or a zwitterionic detergent. The extracted telomerase is used to mediate extension of a telomerase substrate in a telomerase substrate extension reaction. Alternatively, the telomerase activity is detected in situ, where a telomerase substrate is internalized by the cells in a sample and then extended by the telomerase in situ. The extended telomerase substrate is detected by specific hybridization and subsequent extension of an oligonucleotide "primer" complementary to a telomeric repeat sequence. A number of useful reagents of the invention relate to this step. Typically, primer extension is mediated using a template-dependent DNA polymerase, and the primer is extended by addition of nucleotides to the primer by the DNA polymerase.

The DNA polymerase is preferably a thermostable DNA polymerase. Using such a polymerase, one can conduct multiple cycles of primer extension, each cycle comprising the steps of (1) heating the reaction mixture to denature duplex DNA molecules; and (2) cooling the reaction mixture to a temperature at which complementary nucleic acids can hybridize and the polymerase can extend the primer, without inactivating the polymerase. In this embodiment of the method, one can also take advantage of the powerful Polymerase Chain Reaction ("PCR") technology by having an excess amount of the telomerase substrate, which serves as the second primer for the PCR, in the reaction mixture and performing the heating and cooling steps 5, 10, 15, 20, 30, or more times. Alternatively, the primer extension can be mediated by a template-dependent DNA ligase, so that the primer is extended by addition of an oligodeoxyribonucleotide to the primer by the DNA ligase. Typically, the DNA ligase is a thermostable DNA ligase, and the primer extension step is conducted by (1) heating the reaction mixture to denature duplex DNA molecules; and (2) cooling the reaction mixture to a temperature at which complementary nucleic acids can hybridize and the ligase can extend the primer by ligation. In this embodiment of the method, one can also take advantage of the powerful Ligase Chain Reaction ("LCR") technology by having oligonucleotides ("ligomers") complementary to the extended primer in the reaction mixture and by performing the heating and cooling steps from 5, 10, 15, 20, 30, or more times.

The present invention also provides a number of reagents such as oligonucleotides, primers and oligomers, useful in the practice of the present invention. For instance, when one is using PCR to amplify a nucleic acid, one needs to avoid non-specific product formation. Such products can form by a variety of methods, including via interaction of the primers used in the process to form "primer-dimers." The present invention provides primers and reaction conditions designed specifically to minimize the problem of primer-dimer formation.

In another aspect, the invention provides primers that comprise a non-telomeric repeat sequence (a sequence neither identical nor complementary to a telomeric repeat sequence) at the 5'-end of the primer. The use of such primers, called "anchored primers", in the present invention provides a means by which one can assure that the largest primer extension product has no more telomeric repeats than do the largest products of telomerase-mediated extension of the telomerase substrate. Without such primers, multiple cycles of primer extension and product denaturation can yield primer extension products that comprise many more telomeric repeats than present in the telomerase-extended telomerase substrates in the reaction mixture.

The present invention also provides novel configurations of the reagents useful in the telomerase activity assay and kits comprising those reagents to facilitate practice of the method. The activity assay can be conducted in a single reaction tube, which provides a convenient format for packaging the reaction components. For instance, one can prepare the reagents so that the primer is sealed under a wax layer or barrier at the bottom of the tube, and the telomerase substrate and optionally the buffer and polymerase (or ligase) are positioned on top of the barrier. When the tube is heated at the conclusion of the telomerase-mediated telomerase substrate extension step, the wax barrier melts, allowing the primer to mix with the other reaction components. Alternatively, other solid supports, such as glass beads, can be used where the solid support is coated with the primer and encapsulated with wax, thereby separating the primer from other reaction components until heated at the end of the telomerase-mediated telomerase substrate extension step. These formats ensure that the primer will be accessible to the DNA polymerase and any extended telomerase substrates only at temperatures that ensure highly specific nucleic acid base-pairing and so reduces non-specific primer extension and primer-dimer (composed of a primer and an unextended telomerase substrate) formation. Thus, one useful kit of the invention comprises a reaction tube or other solid support having a primer sealed beneath a wax barrier over which the telomerase reaction buffer (optionally comprising a thermostable polymerase or ligase) sits.

The various reagents can also be labelled to facilitate identification of telomerase-extended telomerase substrate. Thus, one can use a labelled nucleoside triphosphate and monitor incorporation of the labelled nucleotides in the telomerase substrate or primer extension products. For more accurate quantification of telomerase activity, however, one can use a labelled telomerase substrate or primer. Any of a wide variety of labels can be used for purposes of the present invention. Such labels typically include fluorescent, phosphorescent, chemiluminescent, enzymatic, and radioactive labels. Alternatively, the label can merely be an unlabelled "tag", which in turn is recognized by a labelled molecule that binds to the tag. For instance, one can use biotin as the tag, use streptavidinylated horseradish peroxidase ("HRP") to bind to the tag, and then use a chromogenic substrate (e.g., 3, 3', 5, 5'-tetramethylbenzidine (TMB) to detect the presence of the HRP. In similar fashion, the tag can be an epitope or antigen, and an enzymatically, a fluorescently, or a radioactively labelled antibody can be used to bind to the tag. The unlabelled tag can also be a branched DNA probe specific for telomeric repeats that can be detected using a labelled probe specific for the branched DNA. Alternatively, an oligonucleotide probe specific for telomeric repeats, the telomerase substrate, or for a portion of both telomeric repeats and telomerase substrate, and labelled with both a fluorescent reporter and a quencher can be used. When included in a primer extension reaction, such as in PCR amplification, the probe is degraded by the 5'-3' exonuclease activity of the polymerase as it extends the primer, thus releasing the fluorescent reporter from the proximity of the quencher and generating a measurable fluorescent signal.

The present invention also provides means other than (or in addition to) a label to provide a quantitative assay for telomerase activity. In this aspect of the invention, a control oligonucleotide or duplex DNA or plasmid with insert consisting essentially of (in the 5'-to-3' direction) the telomerase substrate, a "stuffer" sequence of known length (preferably 3 bases) and composition, a specific number of telomeric repeat sequences, is added in known amounts to the reaction mixture at the beginning of the reaction. Use of this internal control not only facilitates the determination of whether the assay was conducted properly but also facilitates quantification of the telomerase activity present in the sample. The control oligonucleotide, duplex DNA, or plasmid can also be conveniently packaged into a kit with other reaction components.

While the methods of the invention are broadly applicable to the detection of telomerase activity in any sample from any origin, the methods are especially useful and applicable to the detection of telomerase activity in samples of biological material obtained from humans. Such samples will contain cells or cellular materials and will typically be obtained from humans for the purpose of detecting cancer. Telomerase is not expressed by normal post-natal human somatic cells, although low levels of telomerase activity can be detected in certain stem cells and activated cells of the hematopoietic system, so the presence of telomerase activity in a sample of human somatic tissue or cells indicates that immortal cells, including certain types of cancer cells, are present in the tissue. While not all cancer cells express telomerase activity, telomerase expression is required for cells to become immortal. Consequently, the presence of cells with telomerase activity is associated with many forms of cancer and can also serve to indicate that a particularly invasive or metastatic form of cancer is present.

Thus, the invention provides a method for diagnosis of a condition in a patient associated with an elevated level of telomerase activity within a cell. The method involves determining the presence or amount of telomerase activity within the cells of the patient, and the method is therefore applicable to the detection of elevated levels of telomerase activity associated with prostate cancer, breast cancer, colon cancer, renal cancer, skin cancer, liver cancer, ovarian cancer, cervical cancer, lung cancer, urogenitary cancer, and leukemia. The method involves determining the presence or amount of telomerase activity within the cells by a telomerase substrate extension reaction, preferably in conjunction with a primer extension reaction, such as the polymerase chain reaction.

In a further aspect of the invention, an assay system, apparatus and kits are provided which allow for high throughput detection of telomerase activity. The assay system and apparatus provide for simultaneous separation of telomerase products from primers and nucleotides in multiple samples and allows for quantitative detection of the isolated telomerase products. These and other aspects of the invention are described in more detail below.

BRIEF DESCRIPTION OF THE DRAWINGS

The invention will be better understood by reference to the following detailed description of specific embodiments together with the figures that form part of this specification, wherein.

DESCRIPTION OF SPECIFIC EMBODIMENTS

Figure 1A:
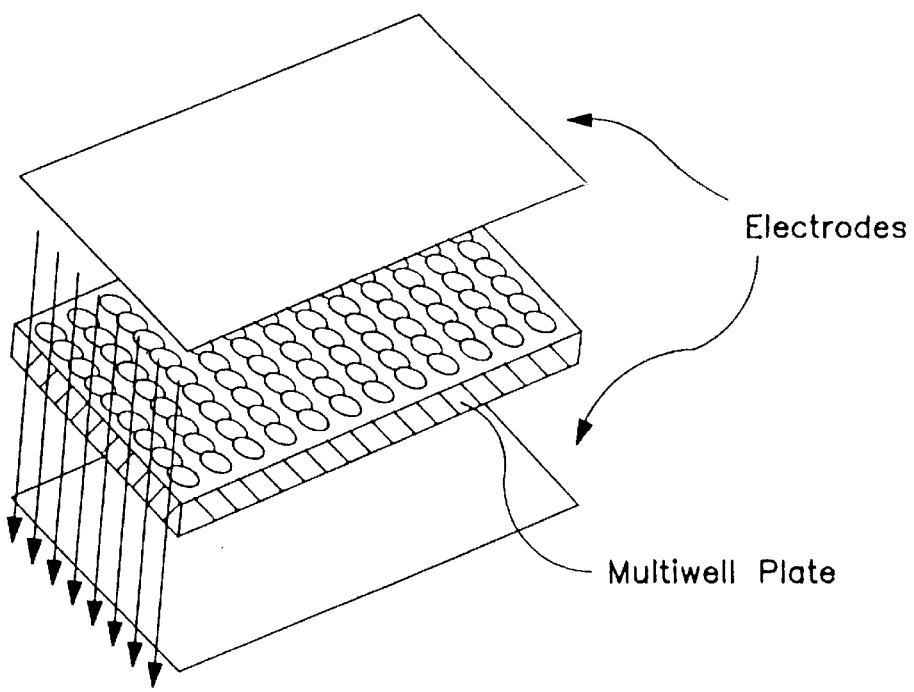
FIG. 1A is a schematic perspective of the Multiplex Electrophoretic Separator (MES) apparatus of the invention. The parallel arrows depict the direction of the electrical field, when the electrodes are attached to the electrical source.

The present invention provides novel methods and materials for the detection of telomerase activity. Telomerase synthesizes telomeric DNA at the ends of chromosomes and is believed to be necessary for indefinite proliferation of immortal cells. Analysis of chromosome terminal restriction fragments in a wide variety of human cell types has shown that telomere length and sequence are stably maintained in immortal cell lines but not in dividing cultures of normal somatic cells. The association of telomerase with immortality has been difficult to establish due to the limited sensitivity of the conventional activity assay, which relies on the incorporation of radioactively-labelled nucleotides into a telomerase substrate to form a labelled telomerase substrate extension product.

The methods of the present invention have been used to test for telomerase activity in human cell lines and normal somatic cells representing 18 different tissues of origin. Extracts from 68 of 68 tumor-derived cell lines, 4 of 6 transformed cell lines, and none of 22 normal somatic cell cultures tested positive for telomerase activity (Example 3 below). The difference in telomerase activity between immortal and normal somatic cells was estimated to be at least 1000-fold. These findings support the direct role for telomerase in telomere dynamics in human cells.

In one embodiment of the invention, telomerase activity is assayed in vitro, requiring the preparation of a cell extract. Methods for the preparation of cell extracts are known in the art (for example, see Scopes, 1987, *Protein Purification: Principles and Practice*, Second Edition, Springer-Verlag, N.Y.). Preferably the detergent lysis method is used which provides more uniform extraction of telomerase even at low cell numbers. The method involves the steps of: (1) collecting a sample of cells; (2) lysing the sample in a lysis buffer comprising 0.01 to 5% of a non-ionic and/or a zwitterionic detergent; (3) removing cellular debris by centrifugation; and (4) collecting supernatant separated from the cellular debris. A wide variety of non-ionic and/or zwitterionic detergents can be employed in the method. Preferred non-ionic detergents include Tween 20, Triton X-100, Triton X-114, Thesit, NP-40, n-octylglucoside, n-dodecylglucoside, n-dodecyl-beta-D-maltoside, octanoyl-N-methylglucamide (MEGA-8), decanoyl-N-methylglucamide (MEGA-10), and isotridecyl-poly (ethyleneglycolether)$_n$, and preferred zwitterionic detergents include CHAPS (3-{(3-cholamidopropyl) dimethylammonio}-1-propane-sulfonate), CHAPSO (3-{(3-cholamidopropyl)dimethyl-ammonio}-2-hydroxy-1- propane-sulfonate, N-dodecyl-N,N-dimethyl-3-ammonio-1-propane-sulfonate, and digitonin, with CHAPS a particularly preferred detergent. While the exact amount of detergent is not critical, 0.5% is typically sufficient to observe the enhanced extraction of telomerase activity.

Example 1, below, demonstrates that CHAPS-extracted telomerase activity functions as expected in the conventional telomerase activity assay. The detergent-extracted activity produces a six nucleotide ladder of extension products characteristic of telomerase activity. A shift in product phase is observed dependent upon the 3'-sequence of the oligonucleotide telomerase substrate, as is expected for telomerase-mediated extension, and the extracted telomerase can extend a non-telomeric oligonucleotide previously shown to be a telomerase substrate (Morin, 1991, *Nature* 353:454–456) with 5'-TTAGGG-3' repeats (as confirmed using dideoxynucleotide chain termination sequencing). The activity was abolished by RNase treatment, as would be expected for telomerase activity (Greider and Blackburn, 1985, *Cell* 43:405–413; Greider and Blackburn, 1989, *Nature* 337:331–337; Morin, 1989, *Cell* 59:521–529). Thus in one aspect of the invention, the method involves the basic steps of:

(a) preparing a cell extract from a cell sample;

(b) placing an aliquot of the cell extract in a reaction mixture comprising a telomerase substrate lacking a telomeric repeat sequence and a buffer in which telomerase can catalyze extension of the telomerase substrate by addition of telomeric repeat sequences;

(c) adding to the reaction mixture a primer comprising a sequence sufficiently complementary to a telomeric repeat to hybridize specifically thereto under conditions such that if an extended telomerase substrate is present in the reaction mixture, the primer will hybridize to the extended telomerase substrate and extend to form a complementary copy of the extended telomerase substrate; and (d) correlating presence of telomerase activity in the cell sample with presence of duplex DNA molecules comprising an extended telomerase substrate bound to an extended primer and absence of telomerase activity in the cell sample with absence of the duplex DNA molecules.

Although the assay of cell extracts is not limited to extracts that have been obtained using the detergent lysis method, such extracts are preferred, especially when only a few cells are available or the number of cells expressing telomerase activity in a sample is very low. The telomerase activity assay of the invention is far superior to the conventional assay in detecting telomerase activity in such circumstances, as well as being faster to complete and more efficient.

In another aspect of the invention, the telomerase activity assay is applied to intact cells. In this embodiment, one treats intact cells with the telomerase substrate oligonucleotide to promote internalization of the substrate, following which the oligonucleotide is extended if the cell possesses functional telomerase activity. Internalization of the substrates can be achieved using methods known in the art, for example, by passive internalization of substrate oligonucleotides or other nucleic acid added to the media surrounding the cell sample (typically at a concentration of 10–100 $\mu$M), by microporation using a detergent or Staphylococcus alpha toxins, by employing liposomes (e.g., LipofectAmine, Lipofectin, LipofectAce), using biolistics, or by electroporation. After the target DNA is internalized by the cell, the sample is incubated to allow any active telomerase present in the cell to extend the substrate by de novo synthesis of telomere repeats. After incubation, the sample is fixed and permeabilized, for example, by treatment with a protease such as proteinase K, pronase, trypsin, pepsin, or the like. The telomerase-extended substrate is then amplified in situ by a primer extension reaction (e.g., employing established PCR or LCR protocols or primed-in situ labeling (PRINS; Koch, J., in "Nonradioactive in situ Hybridization Application Manual" (1992), Boehringer Mannheim, 31–33)) using a labelled nucleotide or oligonucleotide. The presence of a signal in a cell during microscopic examination corresponds to the presence of telomerase activity.

Whether the assay is carried out in vitro or in situ, the method essentially involves two key reactions: (1) telomerase-mediated extension of a telomerase substrate; and (2) a primer extension reaction that proceeds only if telomerase-extended substrates have been produced by telomerase activity present in the sample. For a more complete understanding of the invention, one should first consider some global issues relating to (1) the nature of the sample; (2) the important features of the telomerase substrate; and (3) the nature of the primer extension reaction and the primers and extension reagents used in that reaction.

Any type of sample can be tested by the method. Samples of particular interest include cell samples, which can be tissue or tumor samples, obtained for purposes of diagnostic analysis. The expression of telomerase activity in a variety of cells has been studied and discussed in the scientific literature. Telomerase is expressed not only by pathogens of eukaryotic cells but also by immortal human cells, including certain types of tumor and cancer cells, but is not expressed by cells of normal somatic (as opposed to germline) tissue, although low levels of telomerase activity can be detected in stem cells and in certain activated cells of the hematopoietic system. Consequently, samples might be obtained for the purpose of determining whether a telomerase-expressing pathogen or cancer or tumor cell is present. For such purposes, the sample will often be obtained from a human, but one can also readily understand that samples tested by the present method can be obtained from agriculturally important mammals, such as cattle, horses, sheep, etc., other animals of veterinary interest, such as cats and dogs, and from the environment, for environmental testing for the presence of pathogens.

Regardless of the origin of the sample, in one embodiment of the invention, the practitioner prepares a cell extract, preferably using the detergent-based extraction method of the present invention, and then places that cell extract, or an aliquot of the cell extract, in a reaction mixture comprising a telomerase substrate and a buffer compatible with telomerase activity. Alternatively, telomerase activity is detected in situ after internalization of the telomerase substrate into the cell as described above. The particular telomerase substrate chosen in each case may vary depending on the type or origin of the telomerase activity for which one is testing. The telomerase activity expressed by one organism may differ with respect to substrate specificity from that expressed by another organism. Consequently, if one is using the method to determine whether a cancer cell of human origin is present in the sample, one employs a telomerase substrate recognized by human telomerase.

A variety of substrates are known for the telomerases of Tetrahymena and human cells and can readily be identified for other types of cells. However, when one employs a DNA polymerase-based primer extension step, the present method requires that the telomerase substrate not comprise a telomeric repeat sequence. Those of skill in the art will recognize that the telomeric repeat sequence produced by telomerase activity will depend upon the origin of the telomerase. For instance, Tetrahymena telomerase adds repeats of sequence 5'-TTGGGG-3' to the ends of telomerase substrates, while human telomerase adds repeats of sequence 5'-TTAGGG-3'. Thus, if one is using the present method to assay for human telomerase activity, the telomerase substrate should be a human telomerase substrate lacking the sequence 5'-TTAGGG-3'. There is no requirement that a human telomerase substrate lack a telomeric repeat sequence from an organism that has a telomerase that adds a different repeat, so long as the presence of that different repeat sequence does not produce undesired results, such as excessive primer-dimer formation, as discussed below. For in situ assays, in addition to linear single stranded or duplex nucleic acids, the substrate can be a circular plasmid DNA that undergoes an inducible linearization at a specific site. A plasmid telomerase substrate is a vector that contains an insert with a unique restriction site (e.g.Isce I) 3' to the telomerase substrate sequence. By "unique", it is meant that the restriction site is not present in the genome of the cell under analysis. Preferably, the vector is a mammalian, selectable, multi-copy vector. The system further includes a second expression plasmid that contains a gene coding for a restriction enzyme specific for the unique site, under the control of an inducible promoter. The two plasmids are co-infected into the target cell by methods known in the art, and are replicated. Upon induction of the expression plasmid product, the restriction enzyme cleaves the DNA of the telomerase substrate plasmid at the unique restriction site resulting in a linearized substrate plasmid, the ends of which are recognized as a telomerase substrate and can be elongated with TTAGGG repeats by telomerase.

The requirement for the telomerase substrate to lack telomeric repeat sequences arises out of the second reaction of the present method—the non-telomerase-mediated primer extension reaction. In this reaction, an oligonucleotide primer that hybridizes only to extended telomerase substrates is added to the reaction mixture under conditions such that, if extended telomerase substrates are present, the primer binds to the extended substrates and is then extended by enzymatic action. Because telomerase can extend the telomerase substrate only by the addition of telomeric repeats, the primer will necessarily comprise a sequence complementary to a telomeric repeat. If the telomerase substrate employed in the telomerase extension reaction comprised a telomeric repeat, then the primer employed in the primer extension reaction could hybridize to unextended telomerase substrate, with potentially negative consequences. The telomerase substrate can, however, comprise sequences highly related to a telomeric repeat sequence without compromising the validity of the results obtained. For instance, an especially preferred human telomerase substrate of the invention is oligonucleotide M2, also known as TS, which contains a sequence at its 3'-end that is identical to five of the six bases of the human telomeric repeat but otherwise contains no telomeric repeat sequences.

The primer extension reaction serves to amplify the signal produced by the presence of telomerase activity in a sample (extended telomerase substrates) by producing a second signal (extended primers). The primers can be extended by any means that requires the presence of extended telomerase substrates for primer extension to occur; two preferred means are mediated either by a template-dependent DNA polymerase or a template-dependent DNA ligase. With either of these means, if telomerase activity is present in the sample, an extended telomerase substrate is formed and then hybridizes to a primer, providing a substrate for either DNA polymerase or DNA ligase to produce a primer extension product.

Once a primer extension product has formed, one can disassociate (typically by heating, but one could also use an enzyme or chemical process, such as treatment with helicase) the extended primer from the extended substrate. If additional primer and primer extension reagent is present in the sample, then a new primer/extended telomerase substrate complex can form, leading to the production of another extended primer. One can repeat the process of primer extension and denaturation several to many times, depending upon the amount of signal desired. Typically, primer extension and denaturation of extended primer/extended telomerase substrate complexes will be performed at least 5, 10, 15, 20 to 30 or more times. Moreover, if a second primer complementary to the 3'-end of the extended primer is present in the reaction mixture, one can increase the signal (both extended primer and also additional extended telomerase substrate) dramatically. Unextended telomerase substrate still present in the reaction mixture during the primer extension step could function as such a second primer.

Those of skill in the art will recognize that if the primer extension reagent is a DNA polymerase and a second primer is present, one has the requisite components for a polymerase chain reaction, more fully described in U.S. Pat. Nos. 4,683,195 and 4,683,202, provided the appropriate buffer and nucleoside triphosphates are present in the reaction mixture. PCR amplification is the preferred mode for conducting the primer extension reaction step of the present invention and dramatically increases sensitivity, speed, and efficiency of detecting telomerase activity as compared to the conventional assay. The protocol is termed "TRAP" for Telomeric Repeat Amplification Protocol and is illustrated in Example 2. In this embodiment of the invention, the telomerase substrate also serves as a PCR primer (termed the "upstream primer"). The sequence of the other primer is chosen to avoid annealing of the telomerase substrate and the primer, because even minor levels of primer/telomerase substrate annealing can yield early cycle PCR products identical to telomerase products (e.g., TS plus (5'-AG [GGTTAG]-3')$_n$). In subsequent cycles, these products would serve as template for the production of PCR products, potentially resulting in a false positive.

The present invention provides a variety of oligonucleotide primers and telomerase substrates for use in the PCR-based embodiment of the present invention. One such primer (termed the "downstream primer") is designated "CX" and is composed of sequences complementary to three imperfect telomeric repeats and one perfect repeat, 5'-(CCCTA)$_3$CCCTAA-3' (SEQ ID NO:1). The single nucleotide difference in three of the repeats compromises the capacity of CX to anneal to the telomerase substrate TS (which, as noted above, contains 5 of 6 nucleotides of a telomeric repeat), thereby minimizing the formation of non-specific PCR products, primer-dimer. Any possible alignment between these primers (CX and TS) nucleated by the telomeric sequence complementarily leads to a duplex in which the recessed 3' nucleotide is mismatched and so is not efficiently extended by polymerase.

As the CX primer demonstrates, and as those of skill in the art will recognize upon review of this disclosure, a primer with sequences "complementary to a telomeric repeat" includes a primer that may contain one or more mismatched bases with respect to the telomerase substrate extension product to which the primer is intended to hybridize. The number of mismatches that can be tolerated within this definition can vary depending upon the length and sequence composition of the primer, the temperature and reaction conditions employed during the PCR step, the purpose for which the assay is conducted, and the results desired.

In addition to primer CX, the present invention provides several modifications of a basic PCR that, while not necessary to obtain the benefits of the present method, greatly enhance the specificity, sensitivity, and efficiency of the present method. For instance, one important modification to the in vitro method relates to the buffer: the present invention provides a buffer in which both telomerase activity and DNA polymerase activity can be observed. The use of such a buffer allows the artisan to conduct both the telomerase substrate extension reaction and the primer extension reaction in the same reaction vessel, for example, in a tube (see Example 2).

Another modification relates to the use of short oligonucleotides that are complementary to either the telomerase substrate or the primer in the reaction mixture. These short oligonucleotides are designed to have a melting temperature (with respect to the primer or telomerase substrate to which the short oligonucleotides hybridize) about 10° C. lower than the annealing temperature of the primers used in the primer extension step and to prevent primer-dimer formation and/or non-specific primer extension. The short oligonucleotides melt away from their complementary oligonucleotides at temperatures just below the ideal annealing temperatures for the primer extension step, preventing inappropriate primer extension at lower, non-specific temperatures. If the short oligonucleotide is designed to hybridize to the telomerase substrate, sufficient single-stranded region (about 3 bases) must remain at the 3'-end of the telomerase substrate when hybridized to the short oligonucleotide to allow telomerase-mediated extension to occur. Given that the short oligonucleotides are not intended to serve as primers for DNA synthesis, the 3'-end of the short oligonucleotide can be blocked to prevent addition of nucleotides to the short oligonucleotide. If the short oligonucleotide is designed to hybridize to the primer, then the 3'-end of the short oligonucleotide should be blocked (i.e., with biotin or an amino group) to prevent the short oligonucleotide from serving as a telomerase substrate.

A variety of other reagents and formats can be employed, to ensure a high degree of specificity, including: (1) the use of T4 gene 32 protein (Clontech); (2) the use of a neutralizing monoclonal antibody to Taq DNA polymerase (TAQ START™) antibody; and (3) the separation of the primer from the other reaction components by a wax barrier that melts only after the reaction mixture is heated at the end of the telomerase-mediated extension reaction. For example, the primer can be sealed under a wax layer or barrier at the bottom of a tube with the other reaction components positioned on top of the barrier. Alternatively, other solid matrices can be used, such as polystyrene beads of about 1 micron to about 5 millimeters in diameter available from Abbott Laboratories of North Chicago, Ill.; plates or the wells of a microtiter plate such as those made from polystyrene or polyvinylchloride; glass beads; magnetic particles; polysaccharides; or other surfaces that can be coated with primer. The primer is typically affixed to the solid matrix by adsorption from an aqueous medium although other modes of affixation, well known to those skilled in the art can be used. For example, the solid surface is contacted with a solution of the primer and dried until the surface is coated with an appropriate amount of primer. The amount of primer coated on the solid surface can be varied by adjusting the concentration of primer in solution. The primer-coated solid matrix is then covered with hot molten wax that is left to solidify. The wax barrier thus isolates the primer from the other reaction components until a temperature is reached at which the wax melts. Those of skill in the art will recognize that the reagents employed are commercially available or, in the case of the oligonucleotides, can be prepared using commercially available instrumentation and that a wide variety of DNA polymerases, antibodies, and single-strand DNA binding proteins can be employed in the method.

As shown by the results reported in Example 2, telomerase-positive extracts from human 293 kidney cells were produced routinely from $10^5$ cells, as assessed by TRAP assay, with a lower limit for the conditions employed in the Example of $10^4$ cells for CHAPS extraction. A quantity of extract representing $10^3$ cells (1% of an extract from $10^5$ cells) reproducibly gave a clear positive signal in the TRAP assay with a lower limit for the conditions employed in the Example of $10^2$ cell equivalents for detection of telomerase activity. These results demonstrate at least 100-fold improvements in both extraction efficiency and telomerase activity detection when compared to conventional methods and together increase current detectability of telomerase activity by a factor of $10^4$. Detection in $10^2$ immortal cells and not in $10^5$ BJ cells (a somatic cell culture of skin fibroblasts) indicates that the difference in telomerase activity between immortal and normal somatic cells is at least three orders of magnitude.

Those of skill in the art will recognize the detection limits noted above are valid only if one employs merely routine procedures and that the present method can be used to detect telomerase activity in a single cell, provided one is willing to use effort somewhat greater than what is typically considered routine. For instance, one could increase the time of the telomerase-mediated extension step, increase the amount of labels used in the assay, and increase the number of primer extension cycles to increase the sensitivity of the assay to detect telomerase activity in a few cells or a single cell.

The telomerase activity assay method of Example 2 has been used to test for telomerase activity in various immortal cell lines and normal somatic cell cultures from different tissues and individuals. A comparison of TRAP assays and conventional assays performed on the same 10 cell extracts prepared using the CHAPS detergent lysis method shows activity in both assays with some cell lines (293, MCF-7/ADR-RES, NCI-H23, OVCAR-3, COLO205, M14), while others (AsPC-1 and PC-3) show activity only in the TRAP assay, and the normal somatic cell cultures (BJ, IMR-90 and 31YO) show no detectable activity by either assay. These results demonstrate that the TRAP method can detect telomerase activity in extracts that test negative by the conventional assay.

This survey was expanded to include a total of 74 immortal cell lines and 22 normal somatic cell cultures from 18 different tissues, and the results are summarized in Table 1 (see Example 3, below). None of the normal somatic cell cultures displayed detectable telomerase activity in the TRAP assay. Of the 74 immortal cell lines, 68 were tumor-derived lines and 6 were cell lines transformed with viral oncoproteins. All of the 68 tumor lines contained telomerase activity. Two of the six transformed lines tested negative for telomerase activity. If these two lines are immortal, then the lack of detectable telomerase activity is unexpected. However, an investigation of telomere length in these lines showed that the telomeres were longer than those of the normal somatic cells from which the lines were derived, which may indicate that the cells experienced a transient burst of telomerase activity. If the telomerase activity is not reinitiated, then the cells may not possess unlimited replicative capacity.

The PCR-based embodiment of the present invention offers significant improvements over currently available methods for measuring telomerase activity in a sample. Other novel variations of the present method, however, also offer significant advantages. In particular, the present method can be used to quantitate the telomerase activity in a sample by providing the number of telomerase products generated per unit time. To understand the nature of these improvements, however, one first might consider more carefully the ladder of bands produced upon gel electrophoresis of the assayed samples that extends up the gel. Such results might reflect the number of repeats added by telomerase during the telomerase-mediated extension reaction or could result from staggered binding of primers during PCR amplification.

The phrase "staggered binding" refers to the binding of a primer to a sequence in an extended telomerase substrate in a manner that leaves the 3'-end of the extended telomerase substrate recessed and therefore available for extension by DNA polymerase. DNA polymerase can then add nucleotides to the 3'-end of the extended telomerase substrate, creating molecules longer than those produced in the telomerase-mediated extension step. To determine whether staggered binding was occurring in reactions such as those described in Example 2, synthetic oligonucleotides representing discrete telomerase extension products, e.g., TS+4 (TS plus four telomeric repeats), were used to develop specific amplification conditions. Even under high stringency, staggered annealing of the downstream primer occurred (e.g., annealing by 3 of the 4 repeats). Hence PCR amplification of a discrete telomerase extension product yielded a six nucleotide ladder of PCR products increasing in size up to the limit of gel resolution. Thus, TRAP assay products produced using a primer such as CX are not directly reflective of the length distribution of telomerase products generated in the assay, due to the staggered binding of primers to templates during the primer extension reactions.

In some cases, for example, in in situ telomerase assays, it can be advantageous to have staggered binding resulting in larger molecules that prevent leakage of the telomerase products out of the cell. However, in in vitro assays, it is preferable that such interactions are prevented from generating products with more repeats than telomerase added to the substrate by employing a novel "anchored" primer of the invention as the downstream primer in the assay. The oligonucleotide ACT (see Example 4) is a 24 nucleotide oligonucleotide primer that comprises a 6 nucleotide anchor sequence at its 5'-end and three repeats of CTR (C-rich telomeric repeat) sequence (5'-CTAACC-3'). For purposes of the present invention, an anchor sequence is a 5'-terminal sequence of a PCR primer that is non-complementary and non-identical to a telomeric repeat sequence and that prevents the PCR product from "growing" on itself as observed when the primer pairs TS/(CTR)$_4$ or TS/CX are employed.

A wide variety of anchor sequences can be employed. In one embodiment, the anchor sequence is the sequence of the telomerase substrate used in the telomerase-mediated extension step of the method, providing a "TS-anchored" primer. The anchored primer would thus comprise, in the 5'-to-3' direction, a telomerase substrate sequence and two or more complementary copies of the telomeric repeat sequence. By employing such a primer, one can practice the present method in what is essentially a "one primer" mode, because after the first round of primer extension, excess unextended telomerase substrate in the reaction mixture can prime the synthesis of both strands of the complex formed as a result of the first round of primer extension.

By using the primers TS and ACT (or another anchored primer) in the TRAP assay, one can deduce the Most Processive Product (MPP) of the telomerase in a given extract. The use of an anchored primer such as ACT prevents the growth of telomerase products into longer versions during PCR. With the ACT primer, the slowest migrating band reflects directly the length of the MPP of the original telomerase products before the PCR. The ACT primer is particularly preferred for purposes of the present invention in that it is more resistant to the types of primer-dimer interactions observed between TS and primers such as CX or CTR4. Alternatively, a chimeric oligonucleotide can be used as a return primer. The hybrid has an anchor sequence followed by a primer-based sequence that contains mismatches in the complementary telomeric repeats, for example, ACX 5'-GCGCGGC[TTACCC]$_3$TAACC-3' (SEQ ID NO:2) that has mismatches in 3 of 4 complementary telomeric repeats. This results in a primer that has the ability to destabilize primer-dimer formation (like a CX primer), and has the ability to predict the most processive telomerase product from the TRAP assay (like an ACT primer). Furthermore, the resulting ACX is more resistant to primer-dimer formation than either the ACT or CX primer. The utilization of the ACX primer in the TRAP assay overcomes the need for the wax-barrier methodology in preventing primer-dimer formation, thus simplifying the analysis, manufacture, and performance of the TRAP assay.

The TRAP assay can be further improved by reducing non-specific, template-independent, PCR artifacts (e.g., primer-dimer artifacts) by means other than or in addition to oligonucleotide selection and the use of a hot-start wax barrier. For example, the addition of dimethyl sulfoxide (DMSO), optionally with glycerol, to the TRAP assay buffer destabilizes the interactions between the telomerase substrate primer (e.g., TS) and the return primer (e.g., CX, ACT, etc.) thereby increasing the reliability of the TRAP assay.

While the PCR-based embodiment of the present method has been described in detail above and is exemplified in the Examples below, the present method can be practiced using any method of primer extension. While PCR provides for exponential accumulation of primer extension products, even linear accumulation of primer extension products can provide useful results. Thus, one can use a single primer and merely make many copies of a single strand of the duplex nucleic acid that is produced when PCR is employed.

Moreover, such copies can be made by means other than polymerase-mediated primer extension. Suitable methods include the ligase chain reaction (Barany, 1991, *Proc. Natl. Acad. Sci. USA* 88:189–193), nucleic acid sequence-based amplification (Compton, 1991, *Nature* 350:91–92), self-sustained sequence replication (Guatelli et al., 1990, *Proc. Natl. Acad. Sci. USA* 87:1874–1878), strand displacement amplification (Walker et al., 1992, *Proc. Natl. Acad. Sci. USA* 89:392–396), and branched DNA signal amplification (Urdea, 12 Sep. 1994, *Bio/Tech.* 12:926–928; U.S. Pat. No. 5,124,246), although the latter method involves amplification of the signal produced upon probe hybridization to a target nucleic acid. The assay for detecting telomerase activity with branched DNA (bDNA) can be carried out in a multi-well plate, a format that is particularly useful for screening since the assay is simple to perform for multiple samples and commercial hardware is available. Any telomerase substrate (e.g. TS oligonucleotide 5'-AATCCGTCGAGCAGAGTT-3'; SEQ ID NO:3) can be used and is incubated with a cell extract allowing telomerase to extend the bound substrate with telomeric repeats. In one embodiment, the substrate is linked at its 5' end to a well of a multi-well plate (or other solid surface). The oligonucleotide can be linked to the solid surface using conventional chemical techniques or multi-well plates with linked oligonucleotides are also available commercially (Chiron Corp.). Alternatively, the telomerase substrate is bound by hybridization to a complementary oligonucleotide bound to the solid surface. Thus the telomerase extension reaction can occur on bound oligonucleotide substrate or on free oligonucleotide substrate that is bound at a later stage. The hybridizing portion of branched DNA probe is complementary to the extended telomeric repeats (e.g. 5'-(CCCTAA)$_n$-3' or its permutations) and is hybridized with the immobilized extended substrate. After extensive washing, a labeled secondary probe specific for the branches of the bDNA is hybridized to the bDNA and is detected via the label. Suitable labels are known in the art and include, radioactive, colorimetric, enzymatic, chemiluminescent, and fluorescent labels (e.g. fluorescein-5-isothiocyanate (FITC), rhodamine, etc.). The signal increases in direct proportion to the secondary probe-accessible-sites on the bDNA molecule, thus a rare population of target nucleic acids can be detected by bDNA hybridization. Sensitivity can be further enhanced by probing the telomeric-repeat-complementary-bDNA with a secondary bDNA probe specific for the branches of the primary bDNA probe (and a tertiary probe specific for the secondary probe, etc.), thereby presenting more numerous hybridization sites for the labelled probe used in detection of the final bDNA probe. The use of bDNA to probe for extended telomerase substrates is not limited to use with cell extracts but can also be applied to the in situ methodology of the present invention. Extended telomerase substrates in cells fixed onto a microscope slide, for example, can be probed with bDNA instead of conventional linear nucleic acid molecules. However, in order to facilitate the internalization of the bulky bDNA probes, shorter branch lengths are preferred. Thus, for in situ detection using bDNA, the branches are usually less than about 60 nucleotides in length, preferably less than about 40 nucleotides in length. The improved probe uptake overcomes any decrease in sensitivity of the assay that may occur resulting from shorter branch length. Furthermore, the combination of a secondary bDNA probe specific for the branches of the primary bDNA probe, both bDNA probes having short branches, overcomes any deficiency of the short-branch-bDNA probes. The bDNA methodology could also be applied to the detection of primer extension products, as would be understood by one of skill in the art in light of the above description.

As a further example, DNA ligase can be used to ligate together two oligonucleotides hybridized to a template nucleic acid. If, as in PCR, the duplex nucleic acid is then denatured, then one can repeat the process of ligation and denaturation many times to accumulate many complementary copies of the original template, i.e., the extended telomerase substrate. If one additionally adds two other oligonucleotides complementary to the copy produced by ligation of the first two oligonucleotides on the extended telomerase substrate and selects those oligonucleotides such that DNA ligase can ligate the two together to form a copy of the original extended telomerase substrate, then one has the basic components of an LCR.

To illustrate, one could employ LCR in the present method using the following 4 oligonucleotide "ligomers":

LTS (5'-CCCAATCCGTCGAGCAGAGTTAG-3') (SEQ ID NO:4),
CLT (5'-TAACTCTGCTCGACGGATTCCC-3') (SEQ ID NO:5),
LC (5'-GGGTAACCCTAACCCTAACCC-3') (SEQ ID NO:6), and
LG (5'-GGTTAGGGTTAGGGTTAAA-3') (SEQ ID NO:7).

The LC and CLT ligomers will anneal to an extended telomerase substrate and then be ligated with DNA ligase to form a template for ligation of the LTS and LG ligomers. These ligomers have been selected so that no two ligomers can anneal to form a duplex nucleic acid that can be joined to another duplex nucleic acid in the mixture by the blunt-end ligation activity of DNA ligase. There is no requirement that the telomerase substrate be free of telomeric repeat sequences when the primer extension step of the present method is mediated by a ligase activity. A wide variety of such ligomers can be used in the method to minimize template-independent product formation. LCR amplification of telomerase extension products produces an amplified product of uniform size and so is conducive to quantitative analysis.

The present invention provides a variety of means to quantitate the amount of telomerase in a sample, although for most purposes, a qualitative result (telomerase activity present or absent) is sufficient. One important means for obtaining quantitative information is the use of a control oligonucleotide template added to each reaction mixture in a known amount, as illustrated below in Example 4.

An illustrative control oligonucleotide of the invention comprises, in 5'-to-3' order, a telomerase substrate sequence, a spacer sequence (preferably 3 bases in length, but which can be any sequence of nucleotides or length, and can alter spacing of the ladder produced by electrophoresis of reaction products produced from telomerase positive samples), and a telomeric repeat sequence (typically present in multiple, e.g., 2 to 50 copies). Of course, an oligonucleotide complementary to the control sequence defined above can also serve as the control sequence, and a double-stranded control nucleic acid, or plasmid with a double-stranded nucleic acid insert can also be employed. Use of this internal control not only facilitates the determination of whether the assay was conducted properly but also facilitates quantitation of the telomerase activity present in the sample.

Alternatively, one can add a control nucleic acid of any sequence to the reaction mixture in known amounts and amplify the control with primers different from those used to amplify the extended telomerase substrate. The control oligonucleotide and/or the primers used to amplify the control oligonucleotide can be labelled identically to or differently from the label used to label the telomerase extension products. The control oligonucleotide can also be conveniently packaged into a kit with other reaction components.

Moreover, a variety of different types of oligonucleotides can be used as a control or in the steps of the method. While the discussion above and Examples below illustrate the invention with results obtained using oligodeoxyribonucleotide telomerase substrates, controls, and primers or ligomers and with DNA ligases or polymerases, the present invention is not so limited. Thus, one can employ oligoribonucleotides or oligonucleotides that comprise one or more modified (i.e., synthetic or non-naturally occurring) nucleotides in the primer extension step. In similar fashion, one can employ an RNA polymerase to extend a primer or to copy an extended telomerase substrate and RT-PCR for detection of RNA in vitro or in situ. These and other variations of the present method will be apparent to those of skill in the art upon consideration of this description of the invention.

Regardless of the nature of the primer extension reaction, the various reagents can be labelled to facilitate identification of telomerase-extended telomerase substrates in a reaction mixture. Those of skill in the art will note that while the method of the invention involves the correlation of telomerase activity in a sample with the formation (presence in the reaction mixture) of duplex nucleic acids composed of extended telomerase substrates annealed to extended primers, one can infer the presence of such molecules by the presence of either (1) an extended telomerase substrate; (2) an extended primer; or (3) a duplex nucleic acid comprising both (1) and (2). In any event, however, one will typically make this correlation by detecting the presence of extended telomerase substrates and/or primers via a label incorporated into one or more of the reaction products.

For instance, one can use a labelled nucleoside triphosphate, a labelled primer, or a labelled telomerase substrate (or a combination of the same) and monitor incorporation of the label into telomerase substrate or primer extension products. The control can also be labelled with the same or a different label. Any of a wide variety of labels can be used for purposes of the present invention. Such labels typically include fluorescent, phosphorescent, chemiluminescent, radioactive labels, and various chromophores. Alternatively, the label can merely be an unlabelled "tag", which in turn is recognized by a labelled molecule that binds to the tag. For instance, one can use biotin as the tag, use avidinylated or streptavidinylated horseradish peroxidase ("HRP") to bind to the tag, and then use a chromogenic substrate (e.g., (TMB)) to detect the presence of the HRP. In similar fashion, the tag can be an epitope or antigen, and an enzymatically, a fluorescently, or a radioactively labelled antibody can be used to bind to the tag.

Alternatively, the TAQMAN™ (fluorogenic reporter and quencher) detection system can be employed to determine whether a primer has been extended by action of a DNA polymerase. The system provides a rapid detection method that is non-radioactive and is readily modified to a multiwell system. A target specific probe that possesses at its 5' end a fluorescent reporter dye tag and at its 3' end a quencher dye tag is incorporated into the primer extension reaction (e.g., PCR amplification). The probe hybridizes to the target sequence at an internal site under primer extension conditions and, if the primer is extended by the action of a DNA polymerase, the 5'-3' exonuclease activity of the polymerase degrades the hybridized probe freeing the reporter dye/dNTP from the proximity of the quencher dye. The increase in the free reporter dye/dNTP complex results in an increase in fluorescence that is proportional to the amount of amplified product (Livak et al., (January 1995) Research News, Perkin Elmer Corporation, 1-5; Lee et al., 1993, *Nucl. Acids Res.* 21:3711–3766). In a typical TAQMAN™ (fluorogenic reporter and quencher) PCR application, where the target is generally a double stranded DNA of 100 bp-1 kb in length, selection of three specific hybridization sites (one site for the forward primer, one site for the return primer and one site for the TAQMAN™ (fluorogenic reporter and quencher probe) is easily accomplished. However, in the TRAP assay, the choice of specific hybridization sites available for the TAQMAN™ (fluorogenic reporter and quencher) probe and the two primers is limited. These sites are the telomerase substrate sequence (e.g., TS; 5'-AATCCGTCGAGCAGAGTT-3'; SEQ ID NO:3), and the telomeric repeat sequences (e.g. TTAGGG), or their complementary sequences. For example, a probe that consists of C-rich telomeric repeat (CTR; 5'-CCCTAA-3') sequences can be used. Although TAQMAN™ (fluorogenic reporter and quencher) probes are generally blocked at their 3' end and thus cannot be elongated during PCR amplification, with ACT (or other TRAP return primers) as they hybridize to the same sites which can lead to a reduction in PCR efficiency. Furthermore, because the primer can generate primer-dimer products with TS, the use of hot-start PCR methodology in the assay is preferred in this case, where the probe and return primer are both separated by a wax barrier from the remaining reaction components. Preferably, a TAQMAN™ (fluorogenic reporter and quencher) probe that consists of a sequence complementary to the telomerase substrate is used. Although this probe does not compete with either the forward or return primers, and thus does not result in primer-dimer formation, it forms a duplex with the forward primer (e.g., TS) which can decrease PCR efficiency during exponential amplification. However, telomerase can recognize and extend double-stranded substrates (see Example 10) and the TRAP reaction can proceed in the presence of forward primer-probe duplexes. Alternatively, a TAQMAN™ (fluorogenic reporter and quencher) probe that consists of a sequence complementary to the 3' region of the forward primer, followed by a telomeric repeat sequence (e.g. CTR sequence) can be used. This primer specifically hybridizes to the junction between the forward primer and the telomeric repeat sequence and reduces the competitive effect with the return primer described above, as well as reducing forward primer-probe duplex formation. Using this probe, generation of primer-dimer artifacts can be avoided by using hot-start TRAP methodology. A TAQMAN™ (fluorogenic reporter and quencher) probe consisting of the telomerase substrate sequence or telomere repeat sequences (e.g., TTAGGG) can also be used in the TAQMAN™ (fluorogenic reporter and quencher) detection system. However, in addition to the potential formation of primer-dimers and primer competition discussed above, these probes may compete with the telomerase substrate for telomerase, although this can be overcome by using the hot start methodology described above.

Figure 1B:
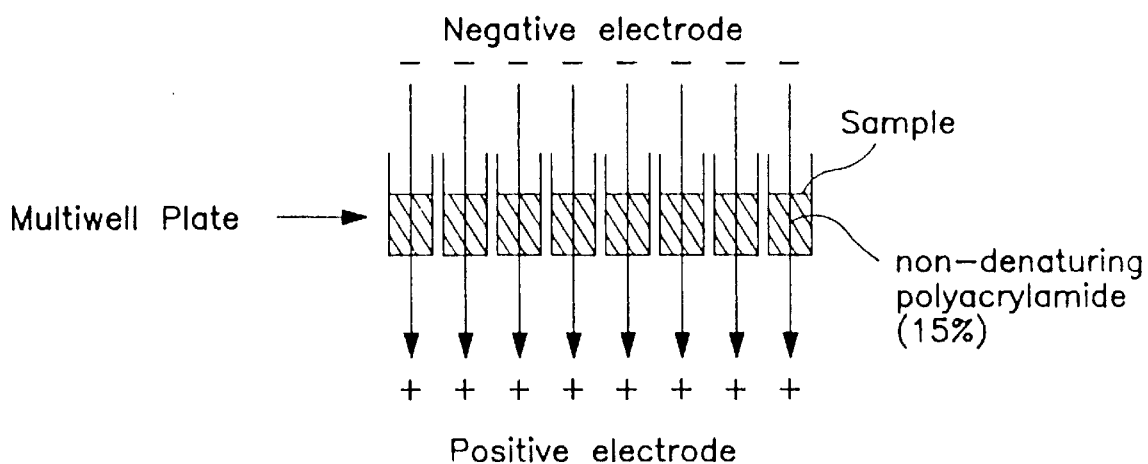
FIG. 1B is a cross sectional view of the apparatus.

Detection of the label may involve additional steps, depending on the needs of the practitioner and the particular label or detection means employed. In some instances, the practitioner may first separate reaction products from one another using gel electrophoresis, as exemplified below. Other separation methods, i.e., chromatography, can also be employed, but for some purposes, no separation will be performed, and the detection of extended telomerase substrates and/or primers will be carried out without removing the reaction mixture from the vessel in which the reaction was performed. One important advantage of the present invention is the adaptability of the method to any detection format of interest. For example, the Multiplex Electrophoretic Separator (MES) has been demonstrated to be useful in analysis of primer extension products or any other samples with a mixture of target nucleic acid and non-specific dNTPs and/or primers (See Example 11) and is particularly useful for high throughput diagnostic assays. The apparatus comprises a housing (1) containing a receptacle (2) adapted to receive a multiwell plate (3), and two electrodes (4). The electrodes are typically parallel to each other and preferably moveably attached to the housing to allow insertion of a multiwell plate onto the receptacle (2) (that retains the multiwell plate between the two electrodes), and have the same configuration as the surfaces of the multiwell plate (i.e., the electrode covers the surface of all wells present in the microtiter plate in preferred embodiments). The multiwell plate typically has 24, 96 or more wells per plate, in single (i.e., a strip of microtiter wells) or multiple rows. Each well (5) is open at its upper surface (6) and has an open but sealable lower surface (7) (e.g., Silent Monitor 96 well plate, Pall Corp., with removable filter bottom, that can be resealed with adhesive tape). The microtiter plate is placed between two electrodes connected to a means for applying an electrical current, such as outlets for connection to a power supply. The electrodes can be made of sheets of any electroconducting material, such as metallic sheets or wire metal grids (FIG. 1). Thus, the apparatus can be used to separate a mixture of compounds in multiple samples by preparing an electrophoretic matrix, such as polyacrylamide or agarose gel, in a sealed well. The seal is removed, the plate is placed in the receptacle (2) above an electrode, and the electrophoretic matrix is immersed in electrophoretic buffer. Alternatively, the buffer contacting the negative and positive electrodes can be provided in two chambers, where the only points of contact between the two chambers is through the electrophoretic matrix. The mixture to be separated is prepared for electrophoresis essentially as for conventional electrophoresis, and then applied to the surface of the electrophoretic matrix. A second electrode is placed above the multiwell plate and both electrodes are connected to a power supply, thus allowing separation of the components of the reaction mixture. Electrophoresis is continued until the non-incorporated dNTPs and primers have eluted from the matrix, after which the MES gel unit is washed and the products inside the matrix detected by an appropriate means for the label used. The label can be radioactive, fluorescent, colorimetric, or enzymatic etc. A combination of these tags could also be used in labeling primers so that different products (e.g., primer extension products of extended telomerase substrates and of control reference) can be detected in a single well.

Having this description of the method and reagents employed, one can consider applications for the telomerase assay of the present invention, which include research and diagnostic applications. Because the assay is fast, simple, and amenable to single reaction vessel reactions, the assay can be used in research and clinical laboratory settings where there is a need to detect telomerase-positive cells. Such applications include, but are not limited to: (i) detection of immortal cells in tumor biopsies for the identification of potential cancer cells; (ii) identification in a cell-based or cell-free screen of agents capable of activating, derepressing, inhibiting, or repressing telomerase, including immortalizing agents (e.g., oncogenes) or compounds that might activate telomerase and extend telomeres and replicative lifespan of cells; (iii) identification in culture systems or in vivo of stem cells or early progenitor cells that possess telomerase activity; (iv) examination of telomerase regulation during differentiation and development; (v) identification of telomerase-positive fractions generated during purification of telomerase; (vi) identification of protozoal or fungal infections; and (vii) diagnosis of certain types of infertility characterized by an absence of telomerase activity.

The diagnostic methods of the present invention can be employed with any cell or tissue type of any origin and can be used to detect an immortal cell of any origin, provided the cell expresses telomerase activity. For human samples, the detection of immortal cells will typically be used to detect the presence of cancer cells of any of a wide variety of types, including without limitation, solid tumors and leukemias including: apudoma, choristoma, branchioma, malignant carcinoid syndrome, carcinoid heart disease, carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell), histiocytic disorders, leukemia (e.g., B-cell, mixed-cell, null-cell, T-cell, T-cell chronic, HTLV-II-associated, lymphocytic acute, lymphocytic chronic, mast-cell, and myeloid), histiocytosis malignant, Hodgkin's disease, immunoproliferative small, non-Hodgkin's lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, sarcoma (e.g., Ewing's, experimental, Kaposi's, and mast-cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia.

In one aspect of the invention, telomerase activity is determined for a urogenitary sample (e.g., biopsy) to diagnose urogenitory cancer, such as bladder cancer. Preferably the cell sample is obtained by collecting a voided urine sample and isolating cells therefrom, for example, by centrifugation, filtration or other physical means. This simple, non-invasive method of obtaining cells for screening prediction of urogenitary cancers is particularly suited to the clinical setting. Telomerase activity can then be assayed, allowing for diagnosis based on the presence of telomerase activity. Any of the current assays for telomerase activity, as well as assays that may be developed in the future can be used. Preferably, the methods described above are used.

In the diagnostic methods of the invention, the assay will be conducted to determine whether an elevated level of telomerase is present. The phrase "elevated level" means that the absolute level of telomerase activity in the particular cell is elevated compared to normal somatic cells in that individual, or compared to normal somatic cells in other individuals not suffering from a disease condition. Generally, any detectable level of telomerase activity is considered elevated in cells from normal, post-natal human somatic tissue. Although telomerase activity is present in germline cells, and low levels of telomerase activity can be detected in stem cells and certain hematopoietic system cells, such cells do not present problems for the practitioner of the present method. Germline cells can be readily distinguished and/or separated from human somatic tissue samples, and the telomerase activity present in stem cells and certain hematopoietic cells is present at such low levels that the few such cells present in somatic tissue samples will not create false positive signals from a telomerase activity assay. The detection of telomerase activity in somatic cells is indicative of the presence of immortal cells, such as certain types of cancer cells, and can be used to make that determination even when the cell would be classified as non-cancerous by pathology. Thus, the method of the present invention allows cancerous conditions to be detected with increased confidence before cells become visibly cancerous.

The diagnostic tests of the invention can also be carried out in conjunction with other diagnostic tests. In some instances, such combination tests can provide useful information regarding the progression of a disease, although the present method for testing for telomerase activity provides much useful information in this regard. When the present method is used to detect the presence of cancer cells in a patient sample, the presence of telomerase activity can be used to determine where a patient is at in the course of progression of the disease, whether a particular tumor is likely to invade adjoining tissue or metastasize to a distant location, and whether an occurrence of cancer is likely to recur. Tests that may provide additional information in conjunction with the present method include diagnostic tests for DNA ploidy, fraction of cells in S-phase, nodal status, Her-2/neu gene products, p53, p16, p21, ras, and other oncogenes.

The present invention also provides kits for performing the diagnostic method of the invention. Such kits can be prepared from readily available materials and reagents and can come in a variety of embodiments. For example, such kits can comprise, in an amount sufficient for at least one assay, any one or more of the following materials: oligonucleotide telomerase substrates (e.g., TS), control reagents (e.g., control oligonucleotides, positive control extracts, etc.), and oligonucleotide primers (e.g., CX, ACT, ACX, LTS, CLT, LC, LG, etc.), optionally provided together with any of the following: reaction vessels, buffers (e.g., cell lysis buffer, end-labelling buffer, TRAP reaction buffer), detergent (e.g., CHAPS, CHAPSO, etc.), nucleotides, labels, enzymes (e.g., polymerase, RNase, polynucleotide kinase), and instructions. Typically, instructions include a tangible expression describing the reagent concentration or at least one assay method parameter such as the relative amounts of reagent and sample to be admixed, maintenance time periods for reagent/sample admixtures, temperature, buffer conditions and the like to allow the user to carry out any one of the assays described above.

In one embodiment of the invention, the kit comprises a reaction tube in which is placed a telomerase substrate and a primer. A preferred form of this kit comprises such a tube in which the primer is separated from other reaction components by a wax barrier. Alternatively, a glass bead or similar structure is provided that has been coated with the primer and a wax barrier. A wide variety of kits and components can be prepared according to the present invention, depending upon the intended user of the kit and the particular needs of the user.

The reagents of any diagnostic assay described herein can be provided in solution, as a liquid dispersion or as a substantially dry power, e.g., in lyophilized form. Where an enzyme or other degradable reagent is provided, conditions are chosen so as to stabilize the reagents, e.g., lower temperature, the addition of stabilizing agents (e.g., glycerol or a reducing agent), etc. The unstable reagents could be provided together with the more stable components of the kit or in a separate package. A solid support such as a multiwell plate, glass beads, or tubes, and one or more buffers can also be included as separately packaged elements in this diagnostic assay system. The kits discussed herein in relation to diagnostic systems are those customarily utilized in diagnostic systems. Such kits include glass and plastic (e.g., polyethylene, polypropylene and polycarbonate) bottles, vials, plastic and plastic-foil laminated envelopes and the like.

The following examples describe specific aspects of the invention to illustrate the invention and provide a description of the present method for those of skill in the art. The examples should not be construed as limiting the invention, as the examples merely provide specific methodology useful in understanding and practice of the invention.

EXAMPLE 1

Preparation of CHAPS-extracted Telomerase

In this Example, cell extracts prepared using the zwitterionic detergent-based extraction method of the invention were tested for telomerase activity using the conventional telomerase assay.

The cell extracts were prepared from immortal 293 cells, which are known to express telomerase activity and are derived from human embryonic kidney cells transformed with fragments of adenovirus type 5 DNA. The cells were grown in Joklik's medium containing 5% to 10% fetal bovine serum and then collected by centrifugation (unless otherwise noted, the procedure below assumes that about $1 \times 10^6$ cells were collected), washed once in PBS, pelleted at 10,000×g for 1 min. at 4° C., and resuspended in 1 ml of ice-cold wash buffer [10 mM HEPES-KOH (pH 7.5), 1.5 mM $MgCl_2$, 10 mM KCl, 1 mM DTT, DEPC-treated water]. The cells were pelleted again and resuspended in ice-cold lysis buffer [10 mM Tris-HCl (pH 7.5), 1 mM $MgCl_2$, 1 mM EGTA, 1 mM PMSF, 5 mM β-mercaptoethanol, DEPC-treated water, 0.5% CHAPS (from Pierce), 10% glycerol] at a concentration of 20 μl of lysis buffer per $10–10^6$ cells (depending on the purpose of the experiment). The suspension was incubated on ice for 30 min. and then spun in a microultracentrifuge at 100,000×g for 30 min. at 4° C. The supernatant was removed to another tube, quick-frozen on dry ice, and stored at −70° C. These extracts typically contained a total protein concentration of 5 to 10 mg/ml, and the telomerase activity was stable to multiple freeze-thaws.

The procedure for and conditions of the conventional telomerase assay were as described by Counter et al., 1992; Counter et al., 1994, *EMBO J.* 11:1921–1929; and Counter et al., 1994, *J. Virol.* 68:3410–3414, using oligonucleotide substrates at a concentration of 1 μM. See also Morin, 1989, *Cell* 59:521–529. The products were separated on an 8% polyacrylamide sequencing gel and exposed overnight to a PHOSPHORIMACER™ storage phosphor screen (Molecular Dynamics, Sunnyvale, Calif.). The telomerase substrates used in the conventional assay were 5'-GTTAGGGTTAGGGTTAGG-3' (abbreviated as "$(GTTAGG)_3$"; SEQ ID NO:8); 5'-TTAGGGTTAGGGTTAGGG-3' (abbreviated as "$(TTAGGG)_3$"; SEQ ID NO:9), and 5=-AATCCGTCGAGCAGAGTT-3' abbreviated as "TS";

SEQ ID NO:3). Control samples were also assayed, which contained extracts pretreated with RNase by incubation of 10 μl of extract with 0.5 μg of RNase (DNase-free, Boehringer Mannheim) for 10 min. at 25° C., which degrades the RNA component of telomerase and abolishes activity. Telomerase pauses after adding the first G of the G triplet, so the number of nucleotides added before the first pause (and thus the phasing of the ladder) is five for $(GTTAGG)_3$ (SEQ ID NO:8), four for $(TTAGGG)_3$ (SEQ ID NO:9), and two for the TS oligonucleotide.

The results demonstrated that the CHAPS-extracted telomerase activity functioned as predicted for human telomerase. The material produced the predicted banding pattern with each of the different telomerase substrates employed, and the banding pattern was abolished with pretreatment of the extract with RNase.

EXAMPLE 2

PCR Amplification of Telomerase Extension Products

This example illustrates the telomerase assay method of the present invention in which a DNA polymerase is used to mediate the primer extension reaction in a polymerase chain reaction. The reaction components include the telomerase substrate TS (the sequence of which is provided in Example 1, above), which telomerase extends by synthesizing telomeric repeats and which also functions as the upstream primer in the PCR step, and the downstream primer CX, the structure of which is defined by its sequence 5'-(CCCTTA)$_3$CCCTAA-3' (SEQ ID NO: 1). Mismatches were designed in the CX primer/extended telomerase substrate to reduce interaction between the CX primer and unextended TS oligonucleotide telomerase substrate and so minimize primer-dimer (more accurately CX primer/TS dimer formation).

As noted above, telomerase is known to extend oligonucleotides of non-telomeric sequence, such as the TS oligonucleotide (Morin, 1991, *Nature* 353:454–456), and oligonucleotide substrate TS was used to avoid non-specific amplification due to PCR primer complementarily. As further modifications to avoid primer interaction, mismatches in the downstream primer CX, single stranded binding protein T4 gene 32 protein, hot start PCR, and an annealing temperature of 50° C. were used to conduct the telomerase activity assays described in this Example. Under these conditions, specific amplification occurs only if the oligonucleotide substrate has been extended with three or more 5'-TTAGGG-3' repeats, resulting in a six nucleotide ladder of TRAP assay products extending from 40 nucleotides (the first amplifiable telomerase product) up to the limit of gel resolution.

Yet another important modification that greatly improves the ease and efficiency of the present method relates to the development of a novel reaction buffer in which both telomerase and DNA polymerase can function. Use of this buffer allows one to employ a single tube set-up or format for the TRAP assay. This modification allows one to increase the specificity of primer extension, because the CX primer is initially separated from the rest of the reaction mix by a wax barrier, which melts only at the higher temperatures that mediate stringent hybridization conditions. The assay tubes were prepared by adding 2 μl of a 50 ng/μl suspension of CX primer (0.1 μg), which was spun to the bottom of the tube and evaporated until dry in a Speed-Vac™ centrifuge.

A trace amount of bromophenol blue was added to the CX primer suspension to monitor possible leakage through the wax barrier prior to thermal cycling. While the addition of dye for this purpose is in no way required for practice of the present invention, dye addition can be a convenient method for monitoring the integrity of a manufacturing process. Tubes were then heated at 70° C., and 7–10 μl of molten wax (Ampliwax™, Perkin-Elmer) was pipetted into the bottom of the tube. After the wax was allowed to solidify at room temperature, the tubes were stored at 4° C. Tubes were warmed to room temperature before use. No effect on assay performance was observed using prepared tubes stored at 4° C. for up to two months; the expected shelf-life of such tubes (and kits comprising the same) is expected to be at least a year.

Reactions were typically carried out by the addition of 50 μl of TRAP reaction solution above the wax barrier. The reaction solution contained 20 mM Tris-HCl, pH 8.3, 1.5 mM $MgCl_2$, 63 mM KCl, 0.005% Tween 20, 1 mM EGTA, 50 mM each dNTP, 0.1 μg of TS oligonucleotide, 0.5 mM T4 gene 32 protein, 0.1 mg/ml BSA, 2 Units of Taq DNA polymerase (optionally use 2 Units of Taq treated with an equal volume of TAQSTART™ neutralizing monoclonal antibody to Taq DNA polymerase available from Clontech to enforce hot start PCR), and 1–2 μl of a CHAPS cell extract. For radiolabeling of products, 0.2 to 0.4 μl of 10 μCi/μl $^{32}$P-dGTP and/or $^{32}$P-dCTP (3000 Ci/mmol) was added to the reaction. After 10 min. at 20° C. for extension of oligonucleotide TS by telomerase, the tubes were transferred to the thermal cycler (96 well Singleblock™ system, Ericomp) for 27 cycles, each cycle comprising incubation temperatures and periods of 94° C. for 30 sec., 50° C. for 30 sec., and 72° C. for 30 sec. to 1.5 min. The CX primer (0.1 μg) was liberated when the wax barrier melted at ~70° C. Those of skill in the art will recognize that the reaction times, temperatures, and buffers described in this Example can vary, depending upon the needs of the practitioner, the particular substrates and primers employed, and the source of the extract and DNA polymerase.

For instance, the telomerase extension reaction can be conducted at temperatures ranging from about 10° to about 42° C., depending upon the source of the telomerase. The telomerase reaction time can vary widely, depending upon the number of primer extension steps employed, the amount of telomerase expected to be in the sample, and the time available to the practitioner. Typically, the telomerase reaction time will be between 5 and 60 min., but the time could be up to several hours. In similar fashion, the PCR cycles can be composed of cycle times and temperatures that vary widely. The simplest PCR cycle comprises a duplex nucleic acid denaturation step followed by a primer annealing and extension step. While denaturation is typically carried out by heating the reaction mixture, other methods, such as helicase treatment, can be used, and the heating method itself can be conducted at a wide range of temperature for any amount of time sufficient to denature but not damage the DNA. In similar fashion, the time and temperature of the primer annealing step depends to a great extent on the reaction buffer and primer sequence, concentration, and composition, as well as the specificity required by the practitioner, while the time and temperature of the primer extension step depends greatly upon the type of DNA polymerase employed. Those of skill in the art will recognize and understand that the present invention is not limited by the times, temperatures, and variations in buffer and other reaction components that can be employed in the method.

For analysis of the samples, one half of the reaction mixture was analyzed by electrophoresis in 0.5×TBE on 15% polyacrylamide non-denaturing gels. Visualization of the products was by ethidium bromide staining, silver staining, SYBR™ Green staining (Molecular Probes) autoradiography, or PHOSPHORIMAGER™ storage phosphor screen analysis (Molecular Dynamics, Sunnyvale, Calif.) of the gels. Control samples were assayed, using: a sample from which the TS oligonucleotide was omitted; a sample from which the cell extract was omitted; a TRAP assay sample of an immortal 293 cell extract; a sample of 293 extract pretreated by incubation for 10 min. at 65° C. to heat-inactivate the telomerase; a sample of 293 extract pretreated by incubation for 10 min. with 0.5 μg of RNase (DNase-free, Boehringer Mannheim) at 25° C. to destroy the RNA component of telomerase; a sample of phenol-extracted 293 extract (by mixing in an equal volume of a 1:1 phenol:chloroform mixture, vortexing for 30 sec., centrifuging to separate the phases, and collecting the aqueous phase); a sample of 293 extract pretreated with protease by incubation of the extract (50 μl) with 5 μg of Bromelain protease (Boehringer Mannheim) for 10 min. at 37° C., removal of the Bromelin protease by incubation with an equal volume of carrier-fixed α2-macroglobulin (Boehringer Mannheim) for 30 min. at 25° C. with shaking and then centrifugation (to pellet the α2-macroglobulin/Bromelain complex) for 10 min. at 10,000×g, and collection of the supernatant for analysis; a normal fibroblast BJ cell extract, which should lack telomerase activity; and a cell extract enriched for telomerase by DEAE chromatography (Morin, 1991, *Nature* 353:454–456).

The results of these multiple control experiments demonstrate that a positive signal in the TRAP (Telomerase Repeat Amplification Protocol) assay requires a ribonucleoprotein in an immortal cell extract capable of extending the TS oligonucleotide with two or more 5'-TTAGGG-3' repeats, validating the assay for specific detection of telomerase activity.

To examine more closely the sensitivity of the TRAP assay, another set of assays was conducted to test the limits of detergent extraction and TRAP detection under the conditions employed. For extraction of different numbers of cells, the volume of lysis buffer was kept constant at 100 μl. No activity was observed in an assay of about $10^5$ cell equivalents from an extract of $10^7$ normal fibroblast BJ cells, as indicated by the absence of the ladder of bands. Telomerase activity was observed in an assay of about $10^4$ cell equivalents from an extract of $10^6$ immortal 293 cells, in an assay of about $10^3$ cell equivalents from an extract of $10^5$ 293 cells, and in an assay of about $10^2$ cell equivalents from an extract of $10^4$ 293 cells. No activity was observed in an assay of about 10 cell equivalents from an extract of $10^3$ 293 cells or in a control assay with lysis buffer only.

The limit of telomerase detection in $10^2$ cells was confirmed by TRAP assays of serial dilutions of an extract from $10^6$ 293 cells. This limit is a function of the TRAP assay conditions employed and should be considered a practical limit under the given set of conditions rather than an absolute limit of the sensitivity of the current method. For instance, use of primers CTR3 [(5'-CCCTAA-3')$_3$ (SEQ ID NO:10)] or CTR4 [(5'-CCCTAA-3')$_4$ (SEQ ID NO:11)] instead of CX further increases sensitivity, although these primers are more likely to interact with the unextended TS primer. The limit of sensitivity was also analyzed by titration of the synthetic telomerase product TS+4 (which contains oligonucleotide TS followed by four telomeric repeats). Dilutions of TS+4 oligonucleotide were mixed with heat-treated (telomerase inactivated) 293 extract and analyzed in TRAP assays. In this analysis, the assay gave a clear positive signal from $10^6$ molecules of TS+4. In addition, telomerase activity from mouse tissue (telomerase activity is present in somatic cells of mice) and cell extracts was detected by TRAP assay even though the mouse telomerase by conventional assay was shown to be mostly non-processive (i.e., adds only a single repeat; Prowse et al., 1993, *Proc. Natl. Acad. Sci. USA* 90:1493–1497), indicating that the TRAP assay is detecting very low levels of processive mouse telomerase activity that cannot be visualized by the conventional assay.

For the convenience of the practitioner, the following product information is provided. Reaction tubes were 0.2 ml Strip-ease™ tubes from Robbins Scientific (Sunnyvale, Calif.) and were autoclaved before use. All oligodeoxyribonucleotides were Ultrapure grade (HPLC-purified) obtained from Keystone Laboratory (Menlo Park, Calif.) and were suspended in DEPC-treated $H_2O$ or TE buffer (10 mM Tris.Cl, pH 7.6; 1 mM EDTA, pH 8.0) at a concentration of 1 mg/ml. Taq DNA polymerase, Tween 20, and T4 gene 32 protein were purchased from Boehringer Mannheim. Radio-isotopes were purchased from NEN-Dupont. The dNTPs were purchased from Pharmacia and were aliquoted, stored at −20° C., and thawed (no more than twice) before use. All other reaction components were molecular biology grade and purchased from Sigma, except when otherwise noted. Diethylpyrocarbonate (DEPC)-treated, de-ionized, sterile $H_2O$ was used routinely.

EXAMPLE 3

Relative Sensitivity of TRAP and Conventional Telomerase Assays—Assay of Telomerase Activity in Normal Somatic and Immortal Cells This Example describes telomerase assays conducted on cell samples of immortal cell lines and normal somatic cell cultures. Adherent cell cultures, such as BJ cells, a normal somatic cell culture of human skin fibroblasts, were grown to 80% confluency prior to extract preparation. The assays ($10^5$ cell equivalents per reaction) were conducted as described in Examples 1 and 2, above, and the results of the assay are summarized in Table 1, below. Assays were performed on the same 10 cell extracts, which were prepared using the CHAPS detergent lysis method (see Examples 1 and 2, above).

Control samples were assayed with extracts pretreated with RNase, which should eliminate any telomerase activity in the sample. The breast carcinoma line MCF-7/ADR-RES, pancreatic carcinoma line AsPC-1, prostatic carcinoma line PC-3, melanoma line M14, normal foreskin fibroblast cell culture BJ, lung carcinoma line NCI-H23, normal stromal fibroblast cell culture 31YO, normal lung fibroblast cell culture, IMR-90, ovarian carcinoma line OVCAR-3, colon carcinoma line COLO205, and immortal kidney cell line 293 were assayed. For conventional assays, $10^6$ cell equivalents were used per reaction.

Some immortal cell lines (293, MCF-7/ADR-RES, NCI-H23, OVCAR-3, COLO205, M14) showed activity in both assays, others (AsPC-1 and PC-3) showed activity only in the TRAP assay, and the normal somatic cell cultures (BJ, IMR-90 and 31YO) showed no detectable activity by either assay. These results demonstrate that the TRAP method can detect telomerase activity in extracts that test negative by the conventional assay.

This survey was expanded to include a total of 74 immortal cell lines and 22 normal somatic cell cultures from 18 different tissues, and the results are summarized in Table 1, below. Each dividing cell culture was detergent-extracted and tested for telomerase activity using the TRAP assay. The specific immortal cell lines and normal somatic cell cultures are listed by tissue of origin. Immortal cell lines and normal somatic cell cultures tested were: (1) Skin—melanoma (LOXIMVI, M14, Malme-3M, UACC-62), normal fibroblasts (GFS, S37b, Malme-3, BJ), normal keratinocytes (primary foreskin); (2) Connective—Fibrosarcoma (HT-1080); (3) Adipose—liposarcoma (SW872); (4) Breast—adenocarcinoma (MCF7, MCF-7/ADR-RES, MDA-MB-231), ductal carcinoma (T 47 D, MDA-MB-435), carcinoma (MDA-MB-157, MDA-MB-175-VI, MDA-MB-436, MDA-MB-468, ZR-75-1, ZR-75-30, UACC-812, UACC-893, BT-20, BT-474, BT-483, BT-549, HS578T, SK-BR-3, SCC70, SCC38, SCC202), normal epithelial and stromal cells (HME: 15, 17, 31, 32, 35); (5) Lung—carcinoma (NCI-H522, NCI-H23, A549, EKVK, 1299, H146, H69, NCI-H460, H358, H182), SV40 T-antigen transformed (IDH4, SW26-IG, SW-26-C4), normal fetal fibroblasts (GFL, IMR-90, Wi38); (6) Stomach—gastric carcinoma (KATO-III); (7) Pancreas—ductal carcinoma (SU.86.86), adenocarcinoma (AsPC-1, Capan-1); (8) Ovary—carcinoma (OVCAR-3, OVCAR-5, IGROV-1), adenocarcinoma (OVCAR-8); (9) Cervix—carcinoma (HeLa S3, C-33 A, HT-3), normal primary epithelial cells; (10) Uterus—normal primary endometrial cells; (11) Kidney—carcinoma (A498, CAKI-1), Ad5-transformed embryonic kidney cells (293); (12) Bladder—carcinoma (5637), transitional cell carcinoma (T24), squamous carcinoma (SCaBER), normal fetal (FHs 738B1); (13) Colon—adenocarcinoma (COLO 205, SW-620, HCT-116); (14) Prostate—adenocarcinoma (PC-3, DU 145), SV40 transformed BPH fibroblasts (BPH-1), normal stromal fibroblasts (31YO), BPH fibroblasts (S52); (15) CNS—carcinoma (U251, SNB-75), glioblastoma (SF268); (16) Blood—leukemia (Molt4, HEL), T-cell leukemia (Jurkats), acute promyelocytic leukemia (HL-60), chronic myelogenous leukemia (K-562), histiocytic lymphoma (U-937); (17) Retina—SV40 transformed pigmented epithelium (AGO6096A); and (18) Joint: normal synovial fibroblast (HSF).

TABLE 1

Telomerase Activity in Mortal and Immortal Cells

| Tissue of Origin | Cell Type (Tumor/ Transformed/ Normal) | Telomerase Activity (# positive/ # tested) |
| --- | --- | --- |
| Skin | Tumor | 4/4 |
|  | Normal | 0/5 |
| Connective | Tumor | 1/1 |
| Joint | Normal | 0/1 |
| Adipose | Tumor | 1/1 |
| Breast | Tumor | 22/22 |
|  | Normal | 0/8 |
| Lung | Tumor | 10/10 |
|  | Transformed | 2/3 |
|  | Normal | 0/3 |
| Stomach | Tumor | 1/1 |
| Pancreas | Tumor | 3/3 |
| Ovary | Tumor | 4/4 |
| Cervix | Tumor | 3/3 |
|  | Normal | 0/1 |
| Uterus | Normal | 0/1 |
| Kidney | Tumor | 2/2 |
|  | Transformed | 1/1 |
| Bladder | Tumor | 3/3 |
|  | Normal | 0/1 |
| Colon | Tumor | 3/3 |
| Prostate | Tumor | 2/2 |
|  | Transformed | 0/1 |

TABLE 1-continued

Telomerase Activity in Mortal and Immortal Cells

| Tissue of Origin | Cell Type (Tumor/ Transformed/ Normal) | Telomerase Activity (# positive/ # tested) |
| --- | --- | --- |
|  | Normal | 0/2 |
| CNS | Tumor | 3/3 |
| Retina | Transformed | 1/1 |
| Blood | Tumor | 6/6 |

None of the normal somatic cell cultures displayed detectable telomerase activity in the TRAP assay. Of the 74 immortal cell lines, 68 were tumor-derived lines and 6 were cell lines transformed with viral oncoproteins. All of the 68 tumor lines contained telomerase activity. Two of the six transformed lines tested negative for telomerase activity. If these two lines are immortal, then the lack of detectable telomerase activity is unexpected. However, an investigation of telomere length in these lines showed that the telomeres were longer than those of the normal somatic cells from which the lines were derived, which may indicate that the cells experienced a transient burst of telomerase activity. If the telomerase activity is not reinitiated, then the cells will not replicate indefinitely.

EXAMPLE 4

Standard Operating Procedure for Telomeric Repeat Amplification Protocol (TRAP)

This Example provides a step-by-step protocol for performing the TRAP assay of the invention, in five parts: (A) Work station set-up; (B) Precautions; (C) Micro-extraction; (D) Quantitative Assay; and (E) Analysis. The method described provides for a quantitative analysis of the activity, and while a number of recommendations are made, those of skill will recognize that, depending on the conditions used and nature of the results desired, not all recommendations need be followed in all circumstances.

A. Work Station Set-up

An important factor in the set-up of the TRAP assay is the environment where the initial reaction mixtures are made prior to the PCR step. The ideal environment is free of contaminating ribonucleases and PCR amplified DNA products, which can cause erroneous negative and positive results, respectively. A major source of PCR product (and RNase) contamination can be the person performing the experiment, who should maintain high standards of personal hygiene and avoid generation of aerosols of PCR products when opening or pipetting PCR products or disposing of gel buffer after the electrophoresis of PCR products. A positive air displacement hood, which blows in filtered air over the sample toward the investigator, is ideal. Separate solutions, pipettes, tubes, and tips should always be used and kept inside the hood. Work space should be wiped with 10% bleach prior to set-up of the reaction, and the hood should be routinely UV-irradiated when not in use. Also, barrels of pipettes should be periodically soaked in 10% bleach, even when aerosol-resistant tips are used. The investigator should wear gloves and a disposable lab coat with elastic wrist straps; the lab coat should be periodically changed.

A dedicated work area for setting up TRAP reaction can be prepared by placing an acrylic shield of 45.7 cm (L)×30.5 cm (W)×61 cm (H) size from VWR (cat. # 56615-848) on a standard cubby-hole type desk. The top of the desk is covered either by a board or heavy cloth, and the front is blocked by the shield. This arrangement creates dead-air space, where the contaminants are prevented from falling into the working area from outside and the samples are physically blocked from the investigator. All the solutions, pipettes, tips, and tubes are kept inside the station, and the working area is routinely UV irradiated by a short-wave UV lamp mounted on the top of the station (Black Ray UV lamp, XX-15S, VWR cat# 36575-059).

(B) Precautions

As noted above, and because the TRAP assay incorporates both PCR amplification and use of in vitro activity of a ribonucleoprotein (telomerase), there is a need for extreme caution to prevent PCR-product contamination (DNA) and RNase contamination, both of which can be detrimental to the assay. The following basic precautions can be followed in all steps of the assay protocol, including the telomerase extraction and PCR amplification steps, to avoid problems: (1) use DEPC-treated $H_2O$ for all solutions, or commercially available nuclease free water (Sigma) and aliquot the solutions in small amounts before use; (2) keep the assay solutions (PCR buffer, CHAPS extraction buffers, dNTPs, Taq polymerase, etc.) separate from other reagents in the laboratory; (3) wear gloves; (4) use a dedicated set of pipettors for the assay and aerosol-resistant tips (ARTs); and (5) do not analyze the amplified samples in the same area where the samples are prepared (i.e., do not open PCR tubes after the PCR amplification on the same bench where the assay reagents and pipettes/tips are located; instead use other pipettors (optionally without ARTs) at a location away from the PCR bench).

(C) Micro-extraction

The material requirements for the lysis buffer used in the micro-extraction procedure are shown below.

| Lysis Buffer (0.5% CHAPS* or CHAPSO*) | | | |
|---|---|---|---|
| Stock | Final | 0.5 mL | 10 mL |
| 1 M Tris-HCl pH 7.5 | 10 mM | 5 µl | 100 µl |
| 1 M $MgCl_2$ | 1 mM | 0.5 µl | 10 µl |
| 0.5 M EGTA | 1 mM | 1 µl | 20 µl |
| *0.1 M PMSF | 0.1 mM | 0.5 µl | 10 µl |
| *βME (14.4 M) | 5 mM | 0.17 µl | 3.5 µl |
| 10% Detergent | 0.5% | 25 µl | 500 µl |
| 100% Glycerol | 10% | 50 µl | 1 mL |
| DEPC $H_2O$ | | 417.83 µl | 8.36 mL |

*The CHAPS or CHAPSO detergent should be added just before use of the lysis buffer. In addition, one should add 0.1 M PMSF (1 µl) and beta-mercaptoethanol (0.35 µl) to 1 ml of lysis buffer just prior to performing the extraction step.

The micro-extraction procedure involves the following steps:
1. Establish the cell count, pellet the cells, wash the cells twice in PBS (Ca and Mg-free), repellet, and remove PBS.
2. Suspend cells in wash buffer and repellet the cells.
3. Remove wash buffer, resuspend cell pellet in 20 µl of lysis buffer per $10^6$–$10^4$ cells (depending on the application).
4. Incubate the cells on ice for 30 min.
5. Spin the cells in a microcentrifuge (Eppendorf) at 10000×g for 20 min. at 4° C.
6. Remove extract to another tube, use 1 to 2 µl per TRAP assay; one can quick-freeze the remainder on dry-ice and store at −70° C, if desired.

(D) Quantitative Assay

The following materials are recommended for the assay: TRAP wax-barrier reaction tubes; ACT primer (5'-GCGCGG[CTAACC]$_3$-3' (SEQ ID NO: 12), 100 ng/tube); 2.5 mM dNTPs (Pharmacia); end-labeled TS Primer (M2, 0.1 mg/ml); Taq polymerase (Boehringer Mannheim); and 10×TRAP Buffer.

| Components | 10X TRAP Buffer For 5 ml |
|---|---|
| 200 mM Tris-HCl, pH 8.3 | 1 ml (1 M Tris-Cl pH 8.3) |
| 15 mM MgCl2 | 75 µl (1 M MgCl2) |
| 630 mM KCl | 3.15 ml (1 M KCl) |
| 0.05% Tween 20 | 25 µl (Boehringer Mannheim) |
| 10 mM EGTA | 500 µl (0.1 M EGTA) |
| 1 mg/ml BSA | 250 µl (20 mg/ml) |
| ACT-IC | 0.77 to 1.54 pg (5–10 amol/50 µl reaction mixture) |

ACT-IC is an internal control oligonucleotide of sequence: 5'-AATCCGTCGAGCAGAGTTAGCCCGGTTAGGGTTA GGGTTAGCCGCGC-3' (SEQ ID NO: 13), specifically designed for the M2 (TS) telomerase substrate (and PCR primer) and the ACT primer. Note that the presence of the sequence complementary to the anchor sequence (5'-CCGCGC-3') is optional and that it may be desirable in some instances not to have this sequence present in the internal control. Presence of this oligonucleotide internal control (the final amount of ACT-IC will be 5-to-10 amol [$10^{-3}$ fmol] per 50 µl TRAP reaction) will result in a specific PCR amplification product that appears as a band on a gel between the first and second products of the TRAP assay, regardless of RNase treatment or no extract control. This internal control band can be used to normalize the PCR amplifications from different samples, and to calculate the number of telomerase products generated when used in combination with end-labeled TS oligonucleotide substrate/primer (see Analysis, below).

To prepare a reaction mixture, the following materials are mixed in the TRAP reaction tube, which contains 0.1 µg of dried ACT primer under a wax barrier.

| Material | For 50 µl Total Volume |
|---|---|
| 10X TRAP Buffer | 5 µl |
| 2.5 mM dNTPs (Pharmacia) | 1 µl |
| *Primer (0.1 mg/ml TS) | 1 µl |
| Taq (Boehringer Mannheim) | 0.4 µl (2 Units) |
| Telomerase Extract | 2 µl |
| $H_2O$ | 40.6 µl |

*For a quantitative TRAP assay, one can end-label the TS substrate/primer with, e.g., [$^{32}$P]-gamma-ATP using T4 polynucleotide kinase, or with other reagents, such as 5'-biotin, digoxigenin, fluorescein or another fluorophore, depending on the particular detection and quantification system to be employed.

Optional ingredients include 0.2 µl of T4 gene 32 protein (5 mg/ml, available from Boehringer Mannheim), and 0.4 µl of TaqStart™ antibody (available from Clontech). The reaction is carried out according to the following steps:
1. incubate the reaction mixture at room temperature (20° C.) for 10 min.;
2. incubate the reaction mixture at the following temperatures for the times indicated to conduct the PCR: 94° C./30 sec., 60° C./30 sec., and 72° C./30 sec.; repeat this three-step cycle to conduct 20–30, preferably 27 cycles;
3. add loading dye containing bromophenol blue and xylene cyanol, and subject samples to 10–15% non-denaturing PAGE in 0.6×TBE, until the bromophenol blue runs off the gel (molecular marker V from Boehringer Mannheim is a good DNA marker for this gel); and
4. observe product formation, e.g., by PHOSPHORIMAGER™ storage phosphor screen (for a radioactive label) or another appropriate means of detection.

(E) Analysis

Using the protocol outlined above and assuming that the internal control is amplified with the same efficiency as the telomerase substrate extension products, one can estimate the number of telomerase product molecules generated in a given reaction, according to the formula (T=total counts per lane):

[(T TRAP Products–T ACT-IC)/T ACT-IC]×(number of molecules of ACT-IC added) The resulting number is the number of molecules of telomerase products generated for a given incubation time (usually 10 min.). This calculation is valid only if the TS substrate was end-labeled and does not apply to a TRAP protocol in which direct incorporation of radioactive dNTPs is used for detection (even if the ACT primer and internal controls are utilized). Alternatively, the amount of telomerase product is quantified by extrapolating the amount of telomerase product by comparing its signal intensity to that of synthetic telomerase product (e.g., 1–10 amol M2R8; 5'-AATCCGTCGAGCAGAGTTAG(GG TTAG)$_7$ SEQ ID NO:14). In this case, the number of telomerase products is determined by the formula:

$$\frac{T \text{ TRAP products} - TACT - IC/TACT - IC}{T \, M2R8 - TACT - IC/TACT - IC} \quad (\# \text{ of molecules of } M2R8)$$

These conditions also account for possible variations in PCR amplification between samples and so provide a standard measurement.

If an extract has high levels of telomerase activity, then the signal from the ACT-IC can be more difficult to detect, because this method involves a "competitive PCR" in which the telomerase products and the internal controls are both competing for the same primers. In other words, the primers should be present in excess over templates for the quantitative analysis to be accurate. Therefore, if a sample has very high levels of telomerase activity, one can dilute the extract so that the PCR primers are not limiting. Alternatively, one can add a control nucleic acid of any sequence to the reaction mixture in known amounts and amplify the control with primers different from those used to amplify the extended telomerase substrate. The control oligonucleotide and/or the primers used to amplify the control oligonucleotide can be labelled identically to or differently from the label used to label the telomerase extension products.

EXAMPLE 5

In Situ Detection of Telomerase Activity

A. Internalization of DNA substrate

Internalization of the substrates can be achieved using passive internalization (target oligos or DNA present in the cell media at conc. of 10–100 μM), microporation by a detergent or Staphylococcus alpha toxins (BRL, following the manufacturer's conditions), liposome (e.g., LipofectAmine, Lipofectin, LipofectAce, from BRL, following the manufacturer's conditions), or by electroporation (e.g., in DMEM media with total volume of 0.8 ml, V=0.25 KV, Capacitance=960 μF, with no resistance in a electroporation cuvette with 0.4 cm gap). After the target DNA is internalized by the cell, the cells are incubated at 37° C. for 1–6 hrs. For solid tissue samples, frozen non-fixed tissue is cut into a thin section on a cryostat, placed on a clean sterile microscopic glass slide and incubated at 37° C. with media containing DNA telomerase substrate, or DNA telomerase substrate with liposomes, for 1–6 hrs. After the incubation, the tissue is gently washed with PBS, and fixed using the methods discussed below. If active telomerase is present, the DNA substrate will be extended with de novo synthesis of TTAGGG repeats.

A plasmid telomerase substrate is a mammalian, selectable, multi-copy vector that contains an insert with a restriction site (e.g., Isce I) that is not present in the mammalian genome, adjacent to the non-telomeric telomerase substrate sequence (e.g., TS sequence, 5'-AATCCGTCGAGCAGAGTT-3') (SEQ ID NO:3). The system also must contain a second expression plasmid that contains a gene coding for the specific restriction enzyme (e.g., Isce I), the promoter of which is under an inducible control, that cuts the unique restriction site present in the insert region of the substrate plasmid. These two plasmids are coinfected into the target cells, and are replicated. Upon induction, the plasmid encoding the unique restriction enzyme expresses the restriction enzyme that will cleave the unique restriction site present only on the insert of telomerase substrate plasmid. This will linearize the substrate plasmid, the ends of which can now be recognized as a telomerase substrate, and elongated with TTAGGG repeats by telomerase.

B. Sample fixation and permeablization

After substrate internalization and incubation, the cells or sectioned tissues are washed twice with PBS and fixed with MeOH:Acetic acid (3:1 ratio, incubated overnight at −20° C.), buffered 10% formalin (4–15 hr at room temperature), 3% paraformaldehyde (4–15 hr at room temperature), 4% formaldehyde (4–15 hr at room temperature), or with commercially available fixative such as Permeafix (ORTHO, 1–5 hr at room temperature). The cells are then fixed onto a microscopic glass slide by CYTOSPIN™ centrifugation and dried overnight at room temperature. The fixed samples are then permeabilized by a protease treatment (e.g., proteinase K, pronase, trypsin, pepsin [2 mg/ml]) for 30–60 min. at room temperature. The samples are washed twice with PBS at room temperature for 10 min, washed briefly with 100% EtOH, and air dried.

C. In situ PCR

Various in situ PCR condition using TS and CTR5 primers ([5'-CCCTAA-3']$_5$) (SEQ ID NO: 15) can be utilized. For example, using the GeneAmp in situ PCR system 1000 and GeneAmp in situ PCR core kit (Perkin Elmer), 50 μl of reaction mix (10 mM Tris-HCl, 50 mM KCl, pH 8.3; 2.5 mM MgCl$_2$; 200 μM dNTPs; 1 μM TS and CTR5 primers; 10 U AmpliTaq DNA polymerase) is added to the sample heated to 70° C., sealed with silicone gasket and clip (following manufacturer's protocol, Perkin Elmer), and amplified for 30 cycles of 94° C./40 sec, 55° C./90 sec. For direct detection of the amplified products, tagged dUTP or primers (tagged by fluorescent labels, radioisotope, biotin, digoxigenin etc., ratio of tagged dUTP to dTTP is 94 μM T-dUTP: 106 μM dTTP) can be incorporated during the PCR amplification. As soon as the last PCR step is completed, the sample is washed 3 times in the wash buffer (4×SSC; 0.05% Tween 20) at 70° C., for 2 min.

To reduce the background signals that can arise from direct incorporation of tagged dNTPs into cellular DNAs, pretreatment of the samples with dNTPs and DNA polymerase (which also include using Taq DNA polymerase) without the primers to fill in gaps, followed by a treatment of ligase (which include the utilization of thermostable ligase, a process that can be combined with Taq DNA polymerase treatment) to heal the nicks in the cellular DNA, can be used prior to the in situ PCR amplification using labeled dNTPs and primers.

D. Signal detection

If the DNA probe was labeled with fluorescent tag or radioisotope, the sample can be mounted in antifade, or developed using photographic emulsion, and viewed under microscope. Digoxigenin labeled probes are detected following the manufacturer's conditions using conjugated anti-digoxigenin antibodies (Boeringer Mannheim). If the probe was labeled with biotin, the slide is blocked with 2×SSC/1% BSA for 10 min. at room temperature, and then the slide is incubated in fluorescently conjugated avidin/2×SSC/1% BSA (final avidin concentration: 5 µg/ml) at room temperature for 1 hr. The slide is then washed 5 min. at room temperature in the following series: 4×SSC, 4×SSC/0.1% Triton X-100, 4×SSC, PN buffer (0.1M of both mono and dibasic sodium phosphate plus 0.1% Nonidet P40). At this point the sample can be mounted in antifade and viewed under microscope. For amplification of the signal, the slide is blocked in PNM buffer (PN buffer plus 5% [w/v] non-fat dried milk) at room temperature for 10 min., and incubated in solution of biotinylated anti-avidin antibody (5 µg/ml) in PNM buffer at room temperature for 20 min. The slide is then washed in the four-step wash series described above, blocked again with PNM buffer, and incubated with fluorescently conjugated avidin (5 µg/ml) in PNM buffer at room temperature for 20 min. The slide is washed again by the four-step wash series, mounted in antifade and the result is viewed under a microscope.

A. Fluorescent in situ hybridization (FISH)

Identification of telomerase positive cells in a mixed population of cells or tissues can be performed by in situ hybridization of labeled probe targetted to telomerase products. A tissue or cell sample fixed onto a microscopic glass slide is permeabilized. First the nucleic acids are denatured by immersing the slides in 70% deionized formamide/2× SSC solution pre-warmed to 70°–74° C. for 2–3 min. The slides are then transferred to ice-cold 70% EtOH, and then to 95% EtOH, and then to 100% EtOH (4 min. in each solution). 100–200 ng (per slide) of the labeled probe (e.g., a plasmid insert consisting of about 500 bp of 5'-TTAGGG-3' repeat sequences labeled with biotin, digoxigenin, radioisotope, or a fluorescent tag) is dried, resuspended in 10 µl of 100% deionized formamide, denatured by incubation at 75° C. for 8 min., and immediately cooled on ice. To this, 10 µl of 2×hybridization buffer (4×SSC; 4×Denhardt's solution; 20% dextran sulfate; 100 mM Tris, pH 7.5) is added. The probe/hybridization mix (20 µl) is added to the fixed sample, overlayed with a coverslip, and the coverslip sealed with rubber cement or nail polish before incubating the sample at 37° C. for 8–48 hr. After hybridization, the coverslip is removed and the sample is washed twice with 2×SSC/50% deionized formamide at 37° C., and then twice with 2×SSC at 37° C. (5 min. per wash). The sample is then viewed under a microscope as described above.

Another variation to the traditional in situ hybridization detection method is primed-in situ labeling (PRINS; Koch, J., in "Nonradioactive in situ Hybridization Application Manual" (1992), Boehringer Mannheim, 31–33). Detection of telomere repeats by PRINS consists of using an oligonucleotide probe specific for telomere repeats and chain elongation incorporating labeled nucleotides.

PRINS mixture (10 µl of (5% (v/v) glycerol; 10 mM Tris-HCl, pH 8.3; 100 mM KCl; 0.05% (w/v) Tween 20; 0.75 mM EGTA; 2.5 mM MgCl$_2$; 0.4 µM return primer [e.g. CTR4]; 200 µM dATP, dGTP, dCTP; 110 µM dTTP; 90 µM labeled dUTP) is placed on the sample, sealed with a coverslip, anchored with nail polish, overlayed with mineral oil, and incubated at 70° C. for 30 min to 3 hr. As soon as the last PCR step is completed, the sample is washed 3 times in wash buffer (4×SSC; 0.05% Tween 20) heated to 70° C., for 2 min, and the signal is then observed as described above.

To reduce the background signals that can arise from direct incorporation of fluorescent tags during the PCR amplication, indirect detection that consists of PCR amplification using non-tagged dNTPs followed by in situ hybridization utilizing a tagged hybridization probe specific for the amplified product can be used. In this method, the signal is amplified by any PCR method without labeled dNTPs or primers, and the amplified product is detected by in situ hybridization following the protocol described above.

B. Application of product extension primer to in situ PCR

The success of in situ PCR depends on the prevention of the amplified products inside the cellular matrix from leaking out of the cell. For this reason, the PCR product is typically larger than 200 bp, preferably larger than 500 bp, and more preferably larger than 700 bp. Alternatively, leakage of PCR products smaller than 200 bp from the cellular matrix can be prevented by incorporation of "bulky" dNTPs (e.g., biotin, fluorescent tag, digoxigenin labeled dUTP) into the PCR product or by incorporation of a product extension primer into the in situ PCR protocol. The method consists of using a primer that contains 3–4 6 bp repetitive sequence (e.g. [5'-TTTCCC-3']$_{3-4}$) (SEQ ID NO: 16 and SEQ ID NO:17) at the 5' end, followed by a sequence that is specific for the target, in combination with an appropriate return primer, and a third primer that consists solely of repetitive sequences (e.g., [5'-TTTCCC-3']$_4$) (SEQ ID NO:17) to amplify the specific target by in situ PCR. The presence of a third primer elongates the PCR product due to its staggered-binding to the 3'-end of the target PCR product. The elongation of the PCR products can be induced by decreasing the annealing temperature of the initial PCR condition.

For example, if the annealing temperature of the first primer to the target sequence is 60° C., the sample is initially amplified for 15–20 cycles of 94° C./45 seconds and 60° C./45 seconds, then amplified for 15–20 cycles of 94° C./45 seconds and 50° C./45 seconds. Lowered anneal temperature in the second PCR step favors the generation of elongated PCR products by increasing the chance of stagger-binding of the third primer to the repetitive sequences. The resulting elongated PCR products are less prone to leakage through the cellular matrix, thus resulting in a better signal retention in in situ PCR analysis.

EXAMPLE 6

Preparation of TRAP Reaction Beads

A primer solution (ACT; 5–10 ng/µg) with a trace amount of bromophenol blue is mixed with clean sterile glass beads (~300 micron in diameter, acid-washed, Sigma). The bromophenol blue was added to monitor possible leakage through the wax barrier prior to thermal cycling. While the addition of dye for this purpose is in no way required for practice of the present invention, dye addition can be a convenient method for monitoring the integrity of a manufacturing process. The mix is dried until the beads are coated with an appropriate amount of dried primers, and the primer-coated beads are then mixed with hot molten wax. While vigorously mixing, the bead/wax mixture is dispensed onto a clean surface by pipetting and then allowed to solidify. One bead droplet is added to a PCR tube and used in a TRAP assay using the conditions described in Example 2.

EXAMPLE 7

Preparation of TRAP Reaction Plug

A primer solution (ACT; 5–10 ng/µl) is mixed with glass beads (~1000 micron in diameter) and dried as described in Example 6. An aliquot of hot molten wax (~5 µl) is placed into a plug mold having a covered lower surface and left to solidify. A bead is placed on top of the hardened wax layer and a second aliquot of hot molten wax (~5 μl) is placed into the mold over the bead, and allowed to harden. The cover of the lower surface is removed and the finished plug is pushed through the mold. One plug per TRAP assay is used instead of conventional reaction tube and the TRAP assay is conducted as described above in Example 2.

EXAMPLE 8

Wax-Free/Hot-Start-Free TRAP Assay

The effect of DMSO titration on the TRAP assay using TS and ACT primers was determined using 293 extracts in TRAP buffer under cold-start conditions (i.e., no wax barrier). Control samples lacked input extract and one set of control samples included a synthetic telomerase product (M2R8; 5'-TS seq-AG(GGTTAG)$_7$-3' SEQ ID NO:14). Each set of samples were assayed with 0, 1, 2, 3, 4, 5, 6, 7, 8, 9 and 10% DMSO. TS and ACT alone produce typical primer-dimer artifacts that correspond to the first and second (sometimes more) TRAP products. As the DMSO concentration was raised, the production of primer-dimer products increased until at a concentration of 5% DMSO, the primer-dimer artifact production was reduced. The addition of 5% DMSO to the TRAP buffer does not seem to have a significant effect on the telomerase activity (as shown in "293" samples), nor on the efficiency of Taq DNA polymerase (as shown in "M2R8" samples). However, at concentrations above 5%, an increase in primer-dimer formation is observed. Thus, addition of DMSO in the TRAP buffer at a concentration of about 5% can help to reduce the formation of primer-dimer artifacts.

The addition of glycerol in combination with DMSO compensates for potential enzyme complex destabilization caused by DMSO. Addition of 5% glycerol to samples assayed in TRAP buffer containing 5% DMSO did not have any significant effect on the reduction of primer-dimers, improvement of Taq activity (R8 samples), or improvement of telomerase activity (293 samples). Therefore, the addition of glycerol is not necessary for TRAP analysis. However, since 5% glycerol has no apparent inhibitory effect on the TRAP assay, addition of glycerol into the TRAP buffer can be beneficial where enzyme stability becomes critical.

II. ACX primer

The ACX return primer (5'-GCGCGGC[TTACCC]$_3$TAACC-3') (SEQ ID NO:2) is a chimeric oligonucleotide that has the anchor sequence of the ACT primer (5'-GCGCGG-3') at its 5' end followed by a CX primer-based sequence that contains mismatches (5'-C[TTACCC]$_3$TAACC-3') SEQ ID NO:18) in 3 of 4 complementary telomeric repeats (5'-TAACCC-3'). TRAP assays were performed essentially as described in Example 2 using 293 extracts with either TS and ACX, or TS and ACT, in the presence of 5% DMSO, without a wax-barrier (i.e., cold-start conditions) and the products were separated on a 15% polyacrylamide gel. Control samples lacked input extract and one set of control samples included a synthetic telomerase product (M2R8; 5'-TS seq -AG[CGGTTAG]$_7$-3' SEQ ID NO:14). Results with no input 293 extract or with synthetic product, showed that the TS and ACT combination resulted in primer-dimer artifacts, whereas no primer-dimer artifacts were observed with TS and ACX primers. In order to test the robustness of the ACX primer, an attempt was made to induce primer-dimer artifact formation with TS primer by incubating the TRAP assay mixture including TS and ACX on ice without a wax-barrier, and then initiating a PCR amplification in a non-preheated thermocycler block. TS and ACX primers consistently showed no primer-dimer artifact formations, but had no effect on the efficiency of the TRAP reaction. Furthermore, the presence of 5% DMSO did not have an effect on the efficiency of the TRAP reaction, and TS and ACX primers were equally resistant to primer-dimer formation in the absence of DMSO. Therefore, the utilization of the TS and ACX primers in the TRAP assay can replace the need for the traditional wax-barrier methodology for the TRAP assay, thus making the analysis, manufacturing, and the performance of the TRAP assay components more reproducible, simple and reliable.

EXAMPLE 9

Telomerase Activity Detection by Branched DNA (bDNA) Probes

Format 1

Multi-well plates with non-telomeric substrate oligonucleotide (TS; 5'-AATCCGTCGAGCAGAGTT-3') (SEQ ID NO:3) bound to the plate at their 5' end, can be obtained from Synthetic Genetics Corp., Chiron Corp., Calif. Cell extracts are prepared as described in Example 1. Telomerase buffer (100 μl; 20 mM Tris-Cl pH 8.3, 1.5 mM MgCl$_2$, 63 mM KCl, 0.05% Tween 20, 1 mM EGTA, 0.1 mg/ml BSA, 50 μM dNTPs) and 5 μl of CHAPS telomerase cell extract are added to TS-bound microtiter plates and incubated for 30 minutes at 25° C. The solution is then removed from the well and the well washed twice with 200 μl of 1×SSC (8.76 g/l NaCl, 4.41 g/l Na citrate, pH7) at room temperature. Fifty microliters of 1×SSC containing ~15 pmol of bDNA probe specific for the telomeric repeats (5'-(CCCTAA)$_{3-N}$-3' (SEQ ID NO:10); Chiron Corp., Calif.) is then added to the well and incubated at ~55° C. for 30 min with gentle shaking. The solution is then removed from the well and the well washed twice with 200 μl of 0.1×SSC at 37° C. Fifty microliters of 1×SSC containing ~50 pmol of FITC-labeled secondary probe (18 mer) specific for the branched arms of the bDNA is then added to the well (U.S. Pat. No. 5,124,246; Urdea, 1994) and incubated at ~55° C. for 30 min with gentle shaking. The solution is removed from the well and the well washed twice with 0.1×SSC at 37° C. before adding 200 μl of 0.1×SSC. Telomerase products are then detected by employing a fluorescent plate reader.

Format 2

Telomerase buffer (100 μl; 20 mM Tris-Cl pH 8.3, 1.5 mM MgCl$_2$, 63 mM KCl, 0.005% Tween 20, 1 mM EGTA, 0.1 mg/ml BSA, 50 μM dNTPs;) containing 15 pmol of TS primer is added to a sterile standard microtiter plate together with 5 μl of CHAPS telomerase cell extract. The plate is incubated for 30 min at 25° C., after which the solution is transferred to a second microtiter plate with complementary TS primers bound by their 5' ends (5'-(AACTCTGCTCGACGGATT)$_{1-N}$ (SEQ ID NO:19), Synthetic Genetics). The second plate is then incubated at ~55° C. for 30 min with gentle shaking before removing the solution from the well and washing the well twice with 200 μl of 1×SSC at 37° C. Fifty microliters of 1×SSC containing ~15 pmol of bDNA probe specific for the telomeric repeats is then added to the well (see above). The plate is incubated at ~55° C. for 30 min with gentle shaking before after which the solution is removed from the well. The well is then washed twice with 200 μl of 0.1×SSC at 37° C. Fifty microliters of 1×SSC containing ~50 pmol of rhodamine-labeled secondary probe specific for the branched arms of the bDNA is then added to the well. After incubating the plate at ~55° C. for 30 min with gentle shaking, the solution is removed and the well is then washed twice with 0.1×SSC at 37° C. Fluorescence is detected using a fluorescent plate reader after addition of 200 µl of 0.1×SSC.

These formats can be easily modified as would be understood by those of ordinary skill in the art. For example, the telomerase reaction can be performed in a complementary TS-bound microtiterplate, thus eliminating the transfer step of Format 2, and the signal can be drastically increased by probing the telomeric repeat-complementary-bDNA by another bDNA probe before probing with the final fluorescent probe.

EXAMPLE 10

TRAP Product Detection by TAQMAN™ (Fluorogenic Reporter and Quencher) Detection System The method consists of detecting extended telomerase substrates using the non-radioactive TAQMAN™ (fluorogenic reporter and quencher) detection system (Perkin Elmer) modified for use in the TRAP asay. The following probes were designed for use in the detection system. A first probe consists of CTR (5'-CCCTAA-3') sequences. The use of this probe is possible when the probe and ACT return primers are both separated by a wax barrier using the hot-start methodology described in Example 2. A second probe that consists of a sequence complementary to the TS telomerase substrate (5'-AATCGTCGAGCAGAGTT-3') (SEQ ID NO:3) does not compete with either the TS or ACT primers, and thus does not result in primer-dimer formation, but can form a duplex with the TS primer which potentially decreases PCR efficiency. Telomerase was demonstrated to recognize and extend the double-stranded substrates as follows: GTSI-1 is a duplex DNA that was constructed by hybridizing an equal amount of M2A telomerase substrate primer (modified TS: 5'-GCCCAATCCGTCGAGCAGAGTTAG-3') (SEQ ID NO:20) with its complementary sequence CM2A (5'-CTAACTCTGCTCGACGGATTGGGC-3') (SEQ ID NO:21). GTSI-1 was used in a TRAP assay with HKC (variation of anchored CTR primer: 5'-CTCGGTACCAAGCTTCTAACCCTAACCCTAACC-3') (SEQ ID NO:22), and 293 extract, under cold-start conditions (i.e., no wax barrier) using conditions essentially as described in Example 2. The TRAP product was observed with this primer combination and was demonstrated to be RNase sensitive. Thus, the assay detects telomerase activity the TRAP reaction proceeds in the presence of a complementary-TS primer.

Modifications to the probe design are easily accomplished by those of ordinary skill in the art. For example, a probe that consists of a sequence complementary to the 3' region of the TS primer, followed by the CTR sequence can be used. This primer specifically hybridizes to the junction between the TS primer and the telomeric repeat sequence which reduces the ACT-probe competitive effect that occurs with the first probe described above, and reduces TS-probe duplex formation. When using this probe, generation of primer-dimer artifacts can be avoided by use of the hot-start TRAP methodology (see Example 2). Similarly, a probe consisting of the TS sequence and TTAGGG repeat can be used in the TAQMAN™ (fluorogenic reporter and quencher) detection system. However, in addition to the potential formation of primer-dimers and primer competition, the probes based on TS and TTAGGG repeats may compete with TS substrate for telomerase.

EXAMPLE 11

Multiplex Electrophoretic Separator (MES)

The Multiplex Electrophoretic Separator (MES) consists of copper sheets with the same configuration as a multiwell plate (FIG. 1). A 15% non-denaturing polyacrylamide gel was prepared in a bottomless multiwell plate temporarily sealed to allow polymerization of the gel. After removal of the seal, the multiplex gel unit was then placed equidistant from the two metal electrodes, and the complete apparatus submerged in electrophoresis buffer (0.5×TBE (0.045M Tris-Borate, 0.001M EDTA)). Radioactively labeled TS primer was used as a substrate in a TRAP assay using 10-fold serial dilutions of 293 cell extracts (from $10^5$–$10^1$ cell equivalents) essentially as described in Example 2. As a control, 5-fold serial dilutions of the synthetic product R8 from 10 fmol–16 amol (see Example 8) were also included. Each assay/dilution was examined in triplicate. Each sample was then loaded onto the top of a well and an electric field was applied across the gel. After separation of the products from non-incorporated dNTPs and primers, the MES gel unit was washed with water and the product inside the gel detected by means of a phosphorimager. Scattering of the radioactivity by the plastic walls of the MES gel unit causes a haziness in the signal; however, MES was able to distinguish negative samples (RNase controls and no extract) from positive samples including diluted samples. Signal detection using dilutions of 293 extract (1×, 0.1×, 0.01× and 0.001×) was linear as was the case for R8 in the first 4 dilutions (1×, 0.1×, 0.01×, and 0.001×) thus demonstrating quantitative analysis by MES. Further dilutions 0.0001×) were at the limit of detection for the selected reaction conditions.

EXAMPLE 12

Method of Detecting Telomerase Activity from Voided Urine Samples Sample preparation and storage Method 1
1. Collect voided urine (30–40 ml) in 50 ml centrifuge tube.
2. Centrifuge at 1000 g for 15 minutes.
3. Carefully discard supernatent so that the pellet is not disturbed.
4. Resuspend pellet in 30 ml of PBS, repellet by centrifugation (step 2), and repeat.
5. Establish cell count by using a Coulter counter or hemocytometer.
6. Resuspend pellet in 1 ml of PBS, transfer to a 1.5 ml centrifuge tube and repellet (step 2).
7. Carefully discard all supernatant.
8. Freeze on dry ice.
9. Ship on dry ice, or store at −80° C.

Method 2
1. Collect voided urine (30–40 ml) in 50 ml centrifuge tube.
2. Add 100% glycerol to the collected urine to a final concentration of 20%, or add 100% DMSO to the collected urine to a final concentration of 10%.
3. Ship on dry ice.
4. Follow steps 2 to 9 of Method 1.

Method 3
1. Collect voided urine and establish cell count by using a Coulter counter or hemocytometer.
2. Filter voided urine (30–40 ml) through a 0.45 micron filter.
3. Pass 50 ml of PBS through the same filter.
4. Seal the filter in a sterile plastic bag, and freeze on dry ice.
5. Ship on dry ice, or store at −80° C.

These non-invasive, simple methods are particularly useful in a clinical setting for collecting cells of the urogenitary tract.

Extraction procedure for pelleted cells
1. Add 20 µl of CHAPS lysis buffer to $1×10^6$ cells or less. If the cell number is not known, add a volume of lysis buffer equal to the packed-cell volume.

2. Follow the standard CHAPS extraction method described in Example 1 to obtain an extract.

Extraction Procedure for cells collected on a filter

Cut the filter into small pieces (~2 mm square).

2. Resuspend the filter pieces in CHAPS lysis buffer (20 µl of CHAPS lysis buffer for 1×10⁶ cells), making sure that the volume of lysis buffer is equal or greater than the packed volume of the filter pieces.

3. Follow the standard CHAPS extraction method described in Example 1 to obtain extract.

TRAP analysis of the urine-derived extract

Use 2–5 µl of the extracts in a standard TRAP assay as described in Example 2 with 30–35 PCR cycles. Sensitivity can be increased by addition of one or more radioactively-labeled dNTPs, in addition to the end-labeled primers. The presence of telomerase activity is correlated to the presence of cancer cells in the urine sample, and is diagnostic of urogenitary cancer.

EXAMPLE 13

TRAP Assay Reagents and Kit Formats

CHAPS Lysis Buffer

Addition of KCl at a concentration of 1 mM, and the increase of the concentration of CHAPS detergent to 3%, in the CHAPS lysis buffer, increases the efficiency of the telomerase extraction 2–5 fold. Furthermore, the use of the more stable benzamidine in place of phenylmethylsulfonyl fluoride (PMSF) as a protease inhibitor, does not affect the efficiency of extraction and the stability of the extact. Thus, a modified CHAPS lysis buffer consisting of 10 mM Tris-Cl, pH 7.5; 1 mM MgCl$_2$; 1 mM EGTA; 0.1 mM Benzamidine; 5 mM β-mercaptoethanol; 0.5–3% CHAPS; and 1 mM KCl can be used for the TRAP assay as an alternative to those described below.

TRAP internal control (TIC)

A plasmid containing an insert with the TS sequence at its 5' end, followed by 150 bp of non-telomeric "stuffer" fragment, followed by 4 repeats of telomeric repeat sequence (5'-GGTTAG-3') can be used as a TRAP internal control that can be incorporated into a TRAP assay kit. This is a competitive internal control that can be included in the 1×TRAP buffer (at a concentration of ~1 fmol/µl), that results in a TRAP product of about 150 bp.

TRAP Kit Formats (enough reagents for 48 or 96 reactions)

Format 1 (TS and ACT)

1. CHAPS lysis buffer (10 mM Tris-Cl, pH 7.5; 1 mM MgCl$_2$; 1 mM EGTA; 0.1 mM Benzamidine; 5 mM β-mercaptoethanol; 0.5% CHAPS)
2. 10×End-labeling buffer (100 mM Tris-OAc; 100 mM MgOAc; 500 mM KOAc)
3. 10×TRAP reaction buffer (200 mM Tris-Cl, pH 8.3; 15 mM MgCl$_2$; 630 mM KCl; 0.05% Tween 20; 10 mM EGTA; 1 mg/ml BSA; 1 fmol/µl TIC)
4. 50×dNTP mix (2.5 mM of dATP, dGTP, dCTP, and dTTP)
5. TS primer (50×concentration, 1 µg/µl)
6. TRAP reaction tubes (0.1 µg ACT sealed with wax)
7. Taq DNA polymerase (5 U/µl)
8. Polynucleotide Kinase (1 U/µl)
9. 293 positive control cell pellet.
10. H$_2$O
11. Gel loading dye The result of a TRAP assay carried out using the above kit can be visualized non-radioactively by staining with ethidium bromide or SYBR™ Green, or by radioactive detection where the investigator supplies a radioactively labeled primer, nucleotide, or the like.

Format 2 (TS and ACX)

1. CHAPS lysis buffer (10 mM Tris-Cl, pH 7.5; 1 mM MgCl$_2$; 1 mM EGTA; 0.1 mM Benzamidine; 5 mM β-mercaptoethanol; 0.5% CHAPS)
2. 10×End-labeling buffer (100 mM Tris-OAc; 100 mM MgOAc; 500 mM KOAc)
3. 10×TRAP reaction buffer (200 mM Tris-Cl, pH 8.3; 15 mM MgCl$_2$; 630 mM KCl; 0.05% Tween 20; 10 mM EGTA; 1 mg/ml BSA; 1 fmol/µl TIC)
4. 50×dNTP mix (2.5 mM of dATP, dGTP, dCTP, and dTTP)
5. TS primer (50×concentration, 1 µg/µl)
6. ACX primer (50×concentration, 1 µg/µl)
7. Taq DNA polymerase (5 U/µl)
8. Polynucleotide Kinase (1 U/µl)
9. 293 positive control cell pellet.
10. H$_2$O
11. Gel loading dye The result of a TRAP assay carried out using the above kit can be visualized non-radioactively by staining with ethidium bromide, or by radioactive detection where the investigator supplies a radioactively labeled primer, nucleotide, or the like.

Format 3 (TS and ACT or ACX)

1. CHAPS lysis buffer (10 mM Tris-Cl, pH 7.5; 1 mM MgCl$_2$; 1 mM EGTA; 0.1 mM Benzamidine; 5 mM β-mercaptoethanol; 0.5% CHAPS);
2. 10×TRAP reaction buffer (200 mM Tris-Cl, pH 8.3; 15 mM MgCl$_2$; 630 mM KCl; 0.05% Tween 20; 10 mM EGTA; 1 mg/ml BSA; 1 fmol/µl TIC)
3. 50×dNTP mix (2.5 mM of dA, dG, dC, and dTTP)
4. TS primer (50×concentration, 1 µg/µl)
5. TRAP reaction tubes (0.1 µg ACT sealed with wax), or ACX primer (50×concentration, 1 µg/µl)
6. Taq DNA polymerase (5 U/µl)
7. 293 positive control cell pellet.
8. H$_2$O The result of a TRAP assay carried out using the above kit can be visualized non-radioactively by staining with ethidium bromide or SYBR™ Green, or by radioactive detection where the investigator supplies a radioactively labeled primer, nucleotide, or the like.

All publications and patent applications mentioned in this specification are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

What is claimed is:

1. A kit for detecting telomerase activity, said kit comprising:
    (a) a telomerase substrate;
    (b) a primer comprising a sequence complementary to a telomeric repeat sequence; and
    (c) instructions.

2. The kit of claim 1, wherein said telomerase substrate lacks a telomeric repeat sequence.

3. The kit of claim 1, wherein said telomerase substrate is 5'-AATCCGTCGAGCAGAGTT-3' (SEQ ID NO:3).

4. The kit of claim 1, wherein said primer is selected from the group consisting of 5'-CCCTTACCCTTACCCTTACCCTAA-3' (SEQ ID NO:1), 5'-GCGCGGCTAACCCTAACCCTAACC-3' (SEQ ID NO:12) and 5'-GCGCGGCTTACCCTTACCCTTACCCTAACC-3' (SEQ ID NO:2).

5. The kit of claim 1, wherein said kit further comprises an oligonucleotide control for primer extension.

6. The kit of claim 5, wherein said control oligonucleotide comprises, in 5'-to-3' order, a telomerase substrate sequence, a spacer sequence and at least two copies of a telomeric repeat sequence.

7. The kit of claim 5, wherein said control oligonucleotide is 5'-AATCCGTCGAGCAGAGTTAG(GGTTAG)$_7$-3' (SEQ ID NO:14).

8. The kit of claim 1, wherein said kit further comprises a cell pellet or a cell extract as a source of telomerase.

9. The kit of claim 1, wherein said kit further comprises a cell lysis buffer and an assay buffer conducive to telomerase activity.

10. The kit of claim 9, wherein said cell lysis buffer is an aqueous buffer of about 10 mM Tris-Cl, pH 7.5; 1 mM MgCl$_2$; 1 mM EGTA; 0.1 mM PMSF or benzamidine; 5 mM β-mercaptoethanol; 0.5% CHAPS and 10% glycerol.

11. The kit of claim 1, wherein said telomerase substrate is 5'-AATCCGTCGAGCAGAGTT-3' (SEQ ID NO:3), said primer is 5'-GCGCGGCTTACCCTTACCCTTACCCTAACC-3' (SEQ ID NO:2) and said kit further comprises an aqueous buffer of about 10 mM Tris-Cl, pH 7.5, 1 mM MgCl$_2$, 1 mM EGTA; 0.1 mM PMSFor benzamidine, 5 mM β-mercaptoethanol, 0.5% CHAPS and 10% glycerol; an aqueous solution of about 200 mM Tris-Cl, pH 8.3, 15 mM MgCl$_2$, 630 mM KCl, 0.05% Tween 20, 10 mM EGTA and 1 mg/ml BSA; a stock solution of dATP, dGTP, dCTP and dTTP; a control oligonucleotide having the sequence 5'-AATCCGTCGAGCAGAGTTAG(GGTTAG)$_7$-3' (SEQ ID NO:14), water and a control cell pellet positive for telomerase activity.

12. A purified preparation of an oligonucleotide wherein said oligonucleotide is selected from the group consisting of 5'-CCCTTACCCTTACCCTTACCCTAA-3' (SEQ ID NO:1), 5'-GCGCGGCTTACCCTTACCCTTACCCTA ACC-3' (SEQ ID NO:2), 5'-AATCCG TCGAGCAGAGTT-3' (SEQ ID NO:3), 5'-GCGCGGCTAACCCTAACCC TAACC-3' (SEQ ID NO:12) and 5'-AATCCGTCGAG CAGAGTTAGGGTTAGGGTTAGGGTTAGGGTTA GGGTTAGGGTTAGGGTTAG-3' (SEQ ID NO:14).

13. A method for determining whether a cell sample contains telomerase activity, said method comprising the steps of:
    (a) collecting a cell sample;
    (b) incubating said cell sample with a reaction mixture comprising a telomerase substrate lacking a telomeric repeat sequence under conditions such that telomerase can catalyze extension of said telomerase substrate by addition of telomeric repeat sequences;
    (c) adding to said reaction mixture a primer comprising a sequence sufficiently complementary to a telomeric repeat to hybridize specifically thereto under conditions such that if an extended telomerase substrate is present in the cell sample mixture, the primer will hybridize to the extended telomerase substrate and extend to form a complementary copy of the extended telomerase substrate, thereby forming duplex DNA molecules comprising an extended telomerase substrate bound to an extended primer; and
    (d) correlating presence of telomerase activity in said cell sample with presence of said extended telomerase substrate and absence of telomerase activity in said cell sample with absence of said extended telomerase substrate.

14. The method of claim 13, wherein said cell sample is treated to promote internalization of said telomerase substrate by cells in said cell sample.

15. The method of claim 13, wherein said telomerase substrate is a plasmid telomerase substrate.

16. The method of claim 13, wherein said cell sample is pretreated by (1) lysing said cell sample in a lysis buffer comprising 0.01 to 5% of a non-ionic and/or a zwitterionic detergent; (2) removing cellular debris by centrifugation; and (3) collecting supernatant separated from the cellular debris.

17. The method of claim 16, wherein said lysis buffer is an aqueous solution having about 10 mM Tris-Cl, pH 7.5, 1 mM $MgCl_2$, 1 mM EGTA; 0.1 mM PMSF or benzamidine, 5 mM β-mercaptoethanol, 0.5% CHAPS and 10% glycerol.

18. The method of claim 16, wherein said reaction mixture comprises an oligonucleotide control for primer extension.

19. The method of claim 2, wherein said control oligonucleotide comprises, in 5'-to-3' order, a telomerase substrate sequence, a spacer sequence and at least two copies of a telomeric repeat sequence.

20. The method of claim 13, wherein said conditions in step (b) comprise incubating said cell sample at from about 10° C. to about 42° C. for 5 to 60 minutes.

21. The method of claim 13, wherein said primer is 5'-GCGCGGCTTAC CCTTACCCTTACCCTAACC-3' (SEQ ID NO:2).

22. The method of claim 13, wherein step (c) further comprises adding to said reaction mixture a template-dependent, thermostable DNA polymerase and incubating said reaction mixture for 20–30 cycles, each of said cycles comprising the steps of (1) heating said reaction mixture to denature said duplex DNA molecules; and (2) cooling said reaction mixture to a temperature at which complementary nucleic acids can hybridize and said primer can extend if extended telomerase substrates are present.

23. The method of claim 22, wherein each cycle comprises incubating said reaction mixture at 94° C. for 30 sec., 60° C. for 30 sec. and 72° C. for 30 sec.

24. The method of claim 22, wherein said reaction mixture is incubated for 30 cycles of 94° C. for 40 sec. and 55° C. for 90 sec.

25. The method of claim 13, wherein said reaction mixture in step (b) further comprises an agent capable of activating, derepressing, inhibiting, or repressing telomerase.

26. The method of claim 13, wherein said cell sample comprises immortal cells, stem cells, early progenitor cells, protozoal cells, fungal cells, germline cells or fetal cells.

27. The method of claim 13, wherein said cell sample is collected from the urogenitory tract.

28. The method of claim 13, wherein said duplex DNA molecules are detected by staining with ethidium bromide, silver or a green fluorescent nucleic acid dye.

29. The method of claim 13, wherein step (c) further comprises adding to said reaction mixture a template-dependent, thermostable DNA polymerase possessing a 5'-3' exonuclease activity, and a probe that will hybridize to said extended telomerase substrate at a site 3' to the primer hybridization site, said probe comprising a fluorescent label and a quencher dye, whereby said probe is degraded by said polymerase during primer extension to release said fluorescent label from the proximity of said quencher dye to generate a measurable fluorescent signal.

30. The kit of claim 1, wherein said primer further comprises a non-telomeric repeat sequence.

* * * * *